Figure 1:
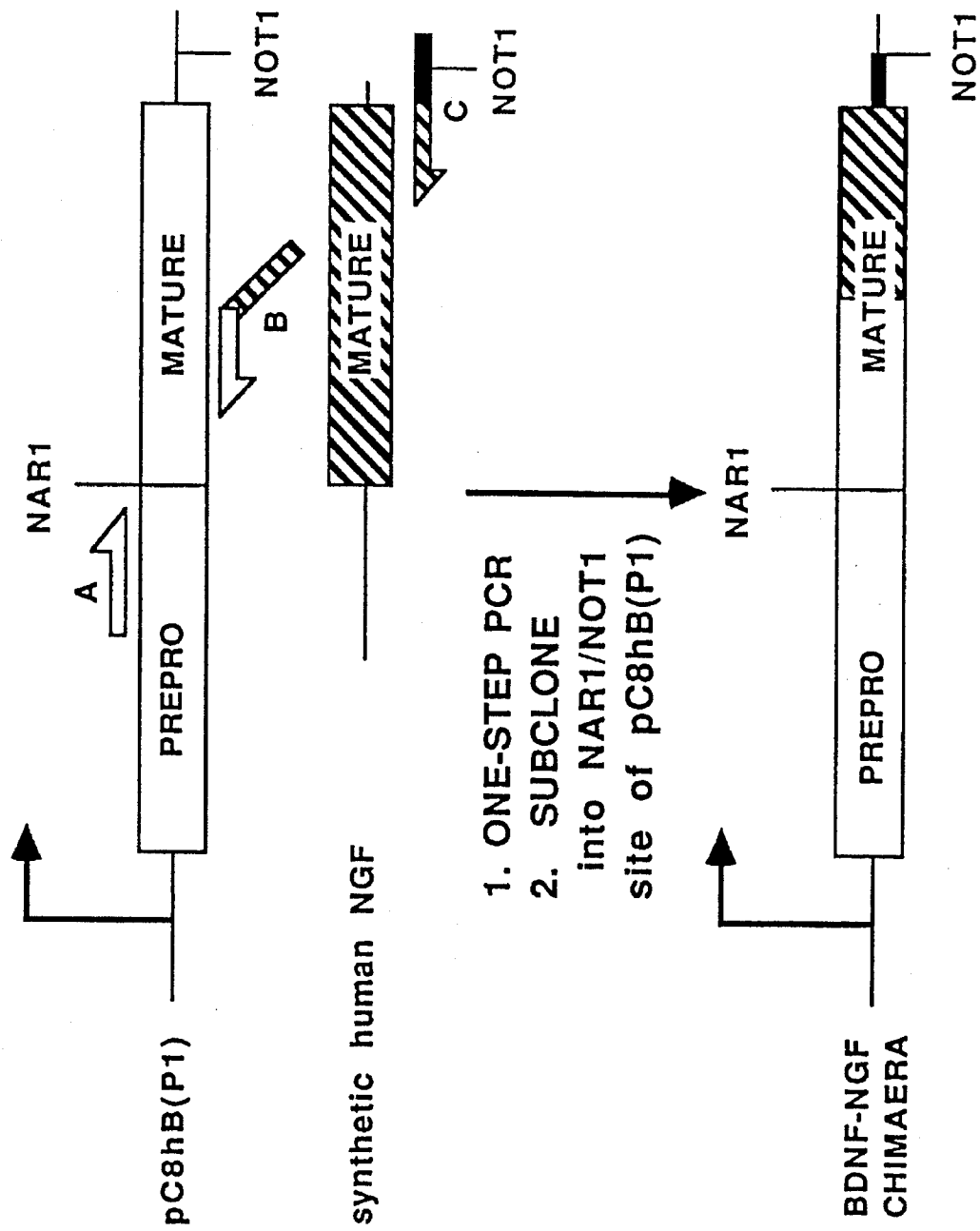

United States Patent [19]

Shooter et al.

[11] Patent Number: 5,512,661
[45] Date of Patent: Apr. 30, 1996

[54] MULTITROPHIC AND MULTIFUNCTIONAL CHIMERIC NEUROTROPHIC FACTORS

[75] Inventors: Eric M. Shooter, Portola Valley; Ulrich Suter, Menlo Park, both of Calif.; Nancy P. Ip, Hong Kong, Hong Kong; Stephen P. Squinto, Irvington, N.Y.; Mark E. Furth, Chapel Hill, N.C.; Ronald M. Lindsay, Briarcliff Manor, N.Y.

[73] Assignee: Regeneron Pharmaceuticals, Inc., Tarrytown, N.Y.

[21] Appl. No.: 308,625

[22] Filed: Sep. 19, 1994

Related U.S. Application Data

[60] Continuation of Ser. No. 923,334, Jul. 31, 1992, abandoned, which is a division of Ser. No. 564,929, Aug. 8, 1990, Pat. No. 5,169,764.

[51] Int. Cl.⁶ .................. C07K 14/475; C07K 14/48; C07K 19/00
[52] U.S. Cl. .............. 530/399; 530/350; 530/839; 930/120
[58] Field of Search .................. 530/350, 399, 530/839; 930/120

[56] References Cited

U.S. PATENT DOCUMENTS

| | | | |
|---|---|---|---|
| 4,855,406 | 8/1989 | Yanaihara et al. | 530/324 |
| 5,134,121 | 7/1992 | Mobley et al. | 514/14 |
| 5,180,820 | 1/1993 | Barde et al. | 435/69.1 |

FOREIGN PATENT DOCUMENTS 0329175  8/1989  European Pat. Off. .

OTHER PUBLICATIONS

Lindsay et al., *Devel. Biol. 112*: 319–328 (1985).
Johnson et al., *J. Neurosci. 6(10)*:3031–3038 (1986).
Lindsay, *J. Neurosci. 8(7)*:2394–2405 (1988).
Ibanez et al., *EMBO J. 9(5)*:1477–1483 (1990).
Scott et al., *Nature 302*: 538–540 (1983).
Ullrich et al., *Nature 303*: 821–825 (1983).
Hohn et al., *Nature 344*: 339–341 (1990).
Kanaya et al., *Gene 83*: 65–74 (1989).
Schulz et al., *Principles of Protein Structure*, pp. 14–16 (1979).
Leibrock et al., *Nature 341*: 149–152, 14 Sep. 1989.
Bernard et al., *EMBO J.2*: 2375–2383, 1983.
Maison Pierre et al., *Science 247*: 1446–1451, 23 Mar. 1990.

*Primary Examiner*—Stephen G. Walsh
*Attorney, Agent, or Firm*—Gail M. Kempler

[57] ABSTRACT

The present invention relates to chimeric neurotrophic factors which comprise at least a portion of a naturally occurring cellular factor and a portion of at least one other molecule such that the resulting chimeric molecule has neurotrophic activity. It is based, in part, on the discovery that chimeric molecules comprising portions of both NGF and BDNF are likely to possess neurotrotrophic activity, and in some cases exhibit a spectrum of activity larger than that of either parent molecule. It is further based on the discovery that chimeric molecules comprising neurotrophic factor sequences as well as additional peptide sequences may retain neurotrophic activity, and in some cases may exhibit a more potent activity than the parent factor. The chimeric neurotrophic factor molecules of the invention provide a number of advantages relative to naturally occurring neurotrophic factors. Chimeric neurotrophic factors may be used to provide, for example, the activity of two neurotrophic factors in a single molecule, or may serve as superagonists of an endogenous neurotrophic factor, thereby enabling an increased biological response at lower doses.

32 Claims, 25 Drawing Sheets

```
                   CLEAVAGE        10            20            30            40            50            60
            <<PREPRO V MATURE>>*        *             *             *             *             *             *
HUMAN NGF   RSKR SSsHPiFHrG EFSVCDSVSV WV--GDKTTATD IKGKEVmVLG EVNINNSVFK QYFFETKCRd
RAT NGF     RSKR SSTHPVFHMG EFSVCDSVSV WV--GDKTTATD IKGKEVmVLG EVNINNSVFK QYFFETKCRA
MOUSE NGF   RSKR SSTHPVFHMG EFSVCDSVSV WV--GDKTTATD IKGKEVTVLa EVNINNSVFr QYFFETKCRA

HUM BDNF    RVRR HS-DPA-RRG ELSVCDSISE WVTAADKKTAVD MSGGTVTVLE KVPVSKGQLK QYFYETKCNP

R1
HUM BDNF    RVRR
HUMAN NGF        SSsHPiFHrG EFSVCDSVSV WV--GDKTTATD IKGKEVmVLG EVNINNSVFK QYFFETKCRd

R2
HUM BDNF    RVRR HS-DPA-RRG ELSVCDS
HUMAN NGF                      VSV WV--GDKTTATD IKGKEVmVLG EVNINNSVFK QYFFETKCRd

R3
HUM BDNF    RVRR HS-DPA-RRG ELSVCDSISE WVTAADKKTAVD MSGGTVTVLE KVPVSKGQLK QYFYETKC
HUMAN NGF                                                                        Rd

R4
HUM BDNF    RVRR HS-DPA-RRG ELSVCDSISE WVTAADKKTAVD MSGGTVTVLE KVPVSKGQLK QYFYETKCNP
HUMAN NGF

R5
HUM BDNF    RVRR HS-DPA-RRG ELSVCDSISE WVTAADKKTAVD MSGGTVTVLE KVPVSKGQLK QYFYETKCNP
HUMAN NGF
```

FIG. 5A

CONTINUED ON FIG. 5B

```
                  70         80         90        100        110        120
             *    *     *    *     *    *     *    *     *    *     *    *
FROM FIG. 5A
PNPVdSGCRG IDSKHWNSYC TTTHTFVKAL TmDgKQ-AAWR FIRIDTACVC VLSRKAvRRa
PNPVESGCRG IDSKHWNSYC TTTHTFVKAL TTDDKQ-AAWR FIRIDTACVC VLSRKAARRG
sNPVESGCRG IDSKHWNSYC TTTHTFVKAL TTDeKQ-AAWR FIRIDTACVC VLSRKAtRRG

MGYTKEGCRG IDKRHWNSQC RTTQSYVRAL TMDSKKRIGWR FIRIDTSCVC TLTIKRGR

PNPVdSGCRG IDSKHWNSYC TTTHTFVKAL TmDgKQ-AAWR FIRIDTACVC VLSRKAvRRa

PNPVdSGCRG IDSKHWNSYC TTTHTFVKAL TmDgKQ-AAWR FIRIDTACVC VLSRKAvRRa

PNPVdSGCRG IDSKHWNSYC TTTHTFVKAL TmDgKQ-AAWR FIRIDTACVC VLSRKAvRRa

MGYTKEGCRG ID
               SKHWNSYC TTTHTFVKAL TmDgKQ-AAWR FIRIDTACVC VLSRKAvRRa

MGYTKEGCRG IDKRHWNSQC R
                        TTHTFVKAL TmDgKQ-AAWR FIRIDTACVC VLSRKAvRRa
```

FIG. 5B

```
R6
  HUM BDNF      RVRR HS-DPA-RRG ELSVCDSISE WVTAADKKTAVD MSGGTVTVLE KVPVSKGQLK QYFYETKCNP
  HUMAN NGF

R7
  HUM BDNF      RVRR HS-DPA-RRG ELSVCDSISE WVTAADKKTAVD MSG**  * *VPVSKGQLK QYFYETKCNP
  MOUSE NGF                                             KEVTVLa E

R8
  HUM BDNF      RVRR HS-DPA-RRG ELSVCDSISE WVTAADKKTAVD MSGGTVTVLE KVP******  QYFYETKCNP
  MOUSE NGF                                                       INNSVFr

R9
  HUM BDNF      RVRR HS-DPA-RRG ELSVCDSISE WVTAADKKTAVD MSGGTVTVLE KVPVSKGQLK QYFYETKC**
  MOUSE NGF                                                                  RA

R10
  HUM BDNF      RVRR HS-DPA-RRG ELSVCDSISE WVTAADKKTAVD MSGGTVTVLE KVPVSKGQLK QYFYETKCNP
  MOUSE NGF

BM1
  HUM BDNF      RVRR HS-DPA-RRG ELSVCDSISE WVTAADKKTAVD MSGGTVTVLE KVPVSKGQLK QYFYETKCNP
  MYC EPITOPE

NM1
  MOUSE NGF     RSKR SSTHPVFHMG EFSVCDSVSV WV--GDKTTATD IKGKEVTVLa EVNINNSVFr QYFFETKCRA
  MYC EPITOPE
```

CONTINUED ON FIG. 5D

FIG. 5C

```
MGYTKEGCRG IDKRHWNSQC RTTQSYVRAL TMDSKKRIGWR FIRIDTSCVC VLSRKAvRRa

MGYTKEGCRG IDKRHWNSQC RTTQSYVRAL TMDSKKRIGWR FIRIDTSCVC TLTIKRGR

MGYTKEGCRG IDKRHWNSQC RTTQSYVRAL TMDSKKRIGWR FIRIDTSCVC TLTIKRGR

******GCRG IDKRHWNSQC RTTQSYVRAL TMDSKKRIGWR FIRIDTSCVC TLTIKRGR
sNPVES

MGYTKEGCRG ID**   *C RTTQSYVRAL TMDSKKRIGWR FIRIDTSCVC TLTIKRGR
           SKHWNSY

MGYTKEGCRG IDKRHWNSQC RTTQSYVRAL TMDSKKRIGWR FIRIDTSCVC TLTI
                                                            GGKDELSTIV sNPVESGCRG IDSKHWNSYC TTHTFVKAL TTDeKQ-AAWR FIRIDTACVC VLSRKAtR
                                                         GGKDELSTIV
```

FIG. 5D

```
                        10          20            30             40
                     *   *       *   *         *   *          *   *
                 v
HUMAN NGF        SSsHPiFHrG  EFSVCDSVSV  WV--GDKTTATD  IKGKEVmVLG
RAT NGF          SSTHPVFHMG  EFSVCDSVSV  WV--GDKTTATD  IKGKEVTVLG
MOUSE NGF        SSTHPVFHMG  EFSVCDSVSV  WV--GDKTTATD  IKGKEVTVLa

HUM BDNF         HS-DPA-RRG  ELSVCDSISE  WVTAADKKTAVD  MSGGTVTVLE

NT-3             YAEH-KSHRG  EYSVCDSESL  WV--TDKSSAID  IRGHQVTVLG

1 MOUSENGF      SS*******G  EFSVCDSVSV  WV--GDKTTATD  IKGKEVTVLA
  HUM BDNF      HSDPARR

2 MOUSENGF      SSTHPVFHM    *    *      --GDKTTATD   IKGKEVTVLA
  HUM BDNF                G ELSVCDSISE  WV

3 MOUSENGF      SSTHPVFHMG  EFSVCDSVSV  WV--*   *    ** KEVTVLA
  HUM BDNF                                 TAADKKTAVD  MSG

4 MOUSENGF      SSTHPVFHMG  EFSVCDSVSV  WV--GDKTTATD  IKG**  *
  HUM BDNF                                             GTVTVLE
```

FIG. 10A

CONTINUED ON FIG. 10B

```
           50         60         70         80         90
            *          *          *          *          *
    EVNINNSVFK QYFFETKCRd PNPVdSGCRG IDSKHWNSYC TTTHTFVKAL
    EVNINNSVFK QYFFETKCRA PNPVESGCRG IDSKHWNSYC TTTHTFVKAL
    EVNINNSVFr QYFFETKCRA sNPVESGCRG IDSKHWNSYC TTTHTFVKAL

KVPVSKGQLK QYFYETKCNP MGYTKEGCRG IDKRHWNSQC RTTQSYVRAL

EIKTGNSPVK QYFYETRCKE ARPVKNGCRG IDDKHWNSQC KTSQTYVRAL

EVNINNSVFR QYFFETKCRA SNPVESGCRG IDSKHWNSYC TTTHTFVKAL

EVNINNSVFR QYFFETKCRA SNPVESGCRG IDSKHWNSYC TTTHTFVKAL

EVNINNSVFR QYFFETKCRA SNPVESGCRG IDSKHWNSYC TTTHTFVKAL

* NINNSVFR QYFFETKCRA SNPVESGCRG IDSKHWNSYC TTTHTFVKAL
    KV
```

FIG. 10B

FROM FIG. 10A

CONTINUED ON FIG. 10C

```
          100            110            120
           *              *              *
       TmDgKQ-AAWR  FIRIDTACVC  VLSRKAvRRa
       TTDDKQ-AAWR  FIRIDTACVC  VLSRKAARRG
       TTDeKQ-AAWR  FIRIDTACVC  VLSRKAtRRG>

TMDSKKRIGWR  FIRIDTSCVC  TLTIKRGR>

TSENNKLVGWR  WIRIDTSCVC  ALSRKIGRT>

TTDEKQ-AAWR  FIRIDTACVC  VLSRKATRRG>

TTDEKQ-AAWR  FIRIDTACVC  VLSRKATRRG>

TTDEKQ-AAWR  FIRIDTACVC  VLSRKATRRG>

TTDEKQ-AAWR  FIRIDTACVC  VLSRKATRRG>
```

FROM FIG. 10B

FIG. 10C 5 (NOTE ASN AT 43)
MOUSENGF
HUM BDNF      SSTHPVF HMG  EFSVCDSVSV  WV--GDKTTATD  IKGKEVTVLA

6 MOUSENGF
HUM BDNF      SSTHPVF HMG  EFSVCDSVSV  WV--GDKTTATD  IKGKEVTVLA

7 MOUSENGF
HUM BDNF      SSTHPVF HMG  EFSVCDSVSV  WV--GDKTTATD  IKGKEVTVLA

8 MOUSENGF
HUM BDNF      SSTHPVF HMG  EFSVCDSVSV  WV--GDKTTATD  IKGKEVTVLA

9 MOUSENGF
HUM BDNF      SSTHPVF HMG  EFSVCDSVSV  WV--GDKTTATD  IKGKEVTVLA

10 MOUSENGF
HUM BDNF      SSTHPVF HMG  EFSVCDSVSV  WV--GDKTTATD  IKGKEVTVLA

11 MOUSENGF
HUM BDNF      SSTHPVF HMG  EFSVCDSVSV  WV--GDKTTATD  IKGKEVTVLA

12 MOUSENGF
HUM BDNF      SSTHPVF HMG  EFSVCDSVSV  WV--GDKTTATD  IKGKEVTVLA

CONTINUED ON FIG. 10E

FIG. 10D

```
EV******** QYFFETKCRA  SNPVESGCRG  IDSKHWNSYC  TTTHTFVKAL
PVSKGQLK

EVNINNSVFR      *  RA  SNPVESGCRG  IDSKHWNSYC  TTTHTFVKAL
        QYFYETKC

EVNINNSVFR QYFFETKC**  ******  RG  IDSKHWNSYC  TTTHTFVKAL
                NP     MGYTKEGC

EVNINNSVFR QYFFETKCRA  SNPVESGC    **       *  TTTHTFVKAL
                               RG  IDKRHWNSQC

EVNINNSVFR QYFFETKCRA  SNPVESGCRG  IDSKHWNSYC  *  ***     *
                                               RTTQSYVRAL

EVNINNSVFR QYFFETKCRA  SNPVESGCRG  IDSKHWNSYC  TTTHTFVKAL

EVNINNSVFR QYFFETKCRA  SNPVESGCRG  IDSKHWNSYC  TTTHTFVKAL

EVNINNSVFR QYFFETKCRA  SNPVESGCRG  IDSKHWNSYC  TTTHTFVKAL
```

FROM FIG. 10D  —  CONTINUED ON FIG. 10F

FIG. 10E

FROM FIG. 10E

```
TTDEKQ-AAWR FIRIDTACVC VLSRKATRRG>
TTDEKQ-AAWR FIRIDTACVC VLSRKATRRG>
TTDEKQ-AAWR FIRIDTACVC VLSRKATRRG>
TTDEKQ-AAWR FIRIDTACVC VLSRKATRRG>

TDEKQ-AAWR FIRIDTACVC VLSRKATRRG>
T

T* * *-**    IRIDTACVC VLSRKATRRG>
 MDSKKRIGWR F

TTDEKQ-AAWR F     *    VLSRKATRRG>
             IRIDTSCVC

TTDEKQ-AAWR FIRIDTACVC * ** **
                       TLTIKRGR
```

FIG. 10F

```
V1                                                                                                    →
    YAEHKSHRGEYSVCDSESLWVT**DKSSAIDIRGHQVTVLGEIKTGNSPVKQYFYETRC    NT-3
    SSTHPVFHMGEFSVCDSVSVWV**GDKTTATDIKGKEVTVLAEVNINNSVFRQYFFETKC   NGF
    HSDPARRGELSVCDSISEWVTAADKKTAVDMSGGTVTVLEKVPVSKGQLKQYFYETKC     BDNF
                                      V2

V3            →                                         V4           →→
    KEARPVKNGCRGIDDKHWNSQCKTSQTYVRALTSENNKLVGWRMRIDTSCVCALSRKIGRT    NT-3
    RASNPVESGCRGIDSKHWNSYCTTTHTFVKALTTDEKQ*AAWRFIRIDTACVCVLSRKATRRG  NGF
    NPMGYTKEGCRGIDKRHWNSQCRTTQSYVRALTMDSKKRIGWRFIRIDTSCVCTLTIKRGR    BDNF
```

FIG. 11

MULTITROPHIC AND MULTIFUNCTIONAL CHIMERIC NEUROTROPHIC FACTORS

This is a continuation of application Ser. No. 07/923,334 filed on Jul. 31, 1992 now abandoned, which is a divisional of application Ser. No. 07/564,929 filed Aug. 8, 1990, now U.S. Pat. No. 5,169,764.

OUTLINE

1. Introduction
2. Background Of The Invention
   2.1. Chimeric Cytokines
   2.2. Neurotrophic Factors
      2.2.1. Nerve Growth Factor
      2.2.2. Brain-Derived Neurotrophic Factor
      2.2.3. Neurotrophin-3
      2.2.4. Ciliary Neurotrophic Factor
3. Summary Of The Invention
4. Description Of The Figures
5. Detailed Description Of The Invention
   5.1. Chimeric Neurotrophic Factors Of The Invention
   5.2. The Construction Of Chimeric Neurotrophic Factors
   5.3. Expression of Chimeric Neurotrophic Factors
   5.4. Neurotrophic Factor Assays For Chimeric Neurotrophic Factors
   5.5. Antibodies Directed Toward Chimeric Neurotrophic Factors
   5.6. Utility Of The Invention
6. Example: Construction And Expression Of BDNF/NGF and MYC-Tagged Chimeric Neurotrophic Factors
   6.1. Materials And Methods
      6.1.1. Construction Of Chimeric Molecules
         6.1.1.1. Construction Of Chimeric Molecules Using A One-Step Polymerase Chain Reaction
         6.1.1.2. Construction Of Chimeric Molecules Using A Three-Step Polymerase Chain Reaction
         6.1.1.3. Construction Of Chimeric Molecules Comprising A MYC "Tag"
      6.1.2. Transfection Of Chimeric Neurotrophic Factor Expression Constructs And Expression In COS Cells
         6.1.2.1. Metabolic Labelling
   6.2. Results And Discussion
7. Example: Neurotrophic Activity Of Chimeric Neurotrophics Factors R1-R10, BM1 And NM1
   7.1. Materials And Methods
      7.1.1. Bioassays Using Tissue Explants
      7.1.2. PC12 Cell Bioassays
   7.2. Results And Discussion
      7.2.1. Explant Assays And Dissociated Cell Cultures
      7.2.2. PC12 Bioassays
8. Example: Construction And Expression Of NGF/BDNF Chimeric Neurotrophic Factors
   8.1. Materials And Methods
      8.1.1. Construction Of Chimeric Molecules
      8.1.2. Expression Of Chimeric Neurotrophic Factors In COS Cells
   8.2. Results And Discussion
9. Example: Neurotrophic Activity Of Chimeric Neurotrophic Factors S1-12
   9.1. Materials And Methods
   9.2. Results
   9.3. Discussion
10. Deposit Of Microorganisms

1. INTRODUCTION

The present invention relates to chimeric neurotrophic factors, molecules which comprise a portion of a naturally occurring factor and a portion of at least one other molecule such that the resulting chimeric molecule has neurotrophic activity. It is based, in part, on the discovery that chimeric molecules comprising portions of two different neurotrophic factors retain substantially full biologic activity and, at least in some cases, possess a unique range of neurotrophic activity in which a single molecule possesses the activity of both parental molecules.

2. BACKGROUND OF THE INVENTION

2.1. CHIMERIC CYTOKINES

Certain cells of the body are capable of producing factors, called cytokines, which act as messengers and communicate with other cells, thereby coordinating biological functions. For example, lymphocytes may produce lymphokines, factors which interact with various components of the immune system in order to effectively orchestrate the immune response. Neurotrophic factors are cytokines which can promote the survival and/or differentiation of components of the nervous system.

As intercellular messengers, cytokines typically interact with specific populations of cells via cytokine receptor molecules. Accordingly, a cytokine is targeted toward particular receptor-bearing cells. It has been shown that cytokines can be used to deliver toxic substances to a cell population by linking the cytokine to the toxic substance. For example, Siegall et al. (1989, Fed. Am. Soc. Exp. Biol. 3:2647–2652) fused a cDNA encoding the cytokine transforming growth factor alpha to the 5' end of a gene encoding a modified form of Pseudomonas exotoxin A which was devoid of the cell recognition domain. The resulting chimeric molecule was expressed in *Escherichia coli*, isolated, and found to be extremely cytotoxic to cells specifically displaying the epidermal growth factor receptor. Ogata et al. (1989, Proc. Natl. Acad. Sci. U.S.A. 86:4215–4219) produced a recombinant chimeric toxin in which the binding cell domain of Pseudomonas exotoxin (PE) was replaced by the murine lymphokine interleukin 4 (IL-4); the chimeric protein, IL-4-PE40, was found to be cytotoxic to murine IL-4 receptor-bearing cell lines. Banker et al. (1989, J. Cell Physiol. 139:51–57) describe an epidermal growth factor-ricin A chain chimera. Williams et al. (1987, Protein Eng. 1:493–498) replaced the diphtheria toxin receptor binding domain with a synthetic gene encoding interleukin 2 (IL-2) and a translational stop signal. The diphtheria toxin/IL-2 fusion protein was found to selectively inhibit protein synthesis in IL-2 receptor bearing cells, whereas cell lines which did not express the IL-2 receptor were resistant to toxin action.

Other investigators have constructed recombinant DNA molecules which comprise a cytokine gene as well as at least a portion of a bacterial gene. Dicou et al. (1989, J. Neurosci. Res. 22:13–19) fused the complete mouse prepro-nerve growth factor DNA to the carboxyl terminus of the beta-galactosidase gene of *Escherichia coli*, and also fused a genomic DNA fragment corresponding to codons 11 to 106 of the human nerve growth factor gene to the fifth codon of the amino terminus of beta-galactosidase. Both bacterial vectors were associated with the expression of large amounts of the chimeric proteins. Although after bacterial cell lysis most of the chimeric mouse prepro-nerve growth factor appeared to be insoluble, the majority of human chimeric beta-nerve growth factor seemed to exist in the supernatant. Neurotrophic activity was not repoted.

In recent studies, Ibanez et al. (1990, EMBO J. 9:1477–1483) describe studies of nerve growth factor altered by site-directed mutagenesis. Xie et al. (1990, Proc. Nat. Acad. Sci. U.S.A. 87:3180–3184) describe the use of chimeric opiod peptides in the study of opiate receptors. Ray et al. (1990, Mol. Endocrinol. 102:101) discuss alteration in receptor binding specificity of growth hormone specificity resulting from genomic exon exchange. Cunningham et al. (1990, Science 247:1330) systematically substituted portions of the growth hormone in order to identify mutant hormones which would be unable to bind to the growth hormone receptor. Cunningham et al. (1990, Science 247:1461) relates to site directed mutagenesis of prolactin observed to produce a prolactin variant capable of binding to the growth hormone receptor.

2.2. NEUROTROPHIC FACTORS

The development and maintenance of the nervous system depends on proteins known as neurotrophic factors. Widespread neuronal cell death accompanies normal development of the central and peripheral nervous systems, and apparently plays a crucial role in regulating the number of neurons which project to a given target field (Berg, D. K., 1982, Neuronal Development 297–331). Ablation and transplantation studies of peripheral target tissues during development have shown that neuronal cell death results from the competition among neurons for limiting amounts of survival factors ("neurotrophic factors") produced in their projection fields. Four important neurotrophic factors identified to date are nerve growth factor (NGF; Levi-Montalcini and Angeletti, 1968, Phys. Rev. 4.8:534); Neurotrophin-3 (NT-3; Hohn et al., 1990, Nature 344:339; Maisonpierre et al., 1990, Science 247:1446), brain-derived neurotrophic factor (BDNF; Barde et al., 1982, EMBO J. 1:549), and ciliary neurotrophic factor (CNTF; Lin et al., 1979, Science 246:1023).

2.2.1. NERVE GROWTH FACTOR

Nerve growth factor (NGF) is by far the most fully characterized of these neurotrophic molecules and has been shown, both in vitro and in vivo, to be essential for the survival of sympathetic and neural crest-derived sensory neurons during early development of both chick and rat (Levi-Montalcini and Angeletti, 1963, Develop. Biol. 7:653–659; Levi-Montalcini et al., 1968, Physiol. Rev. 48:524–569). Injections of purified NGF into the developing chick embryo have been found to cause increase in survival and hypertrophy of spinal sensory neurons and sympathetic neurons (Levi-Montalcini and Booker, 1960, Proc. Natl. Acad. Sci. U.S.A. 46:373–384; Hamburger et al., 1981, J. Neurosci. 1:60–71). Conversely, removal or sequestration of endogenous NGF by daily injection of anti-NGF antibodies into neonatal rats has been associated with virtual destruction of the sympathetic nervous system (Levi-Montalcini and Booker, 1960, Proc. Natl. Acad. Sci. 46:384–391; Levi-Montalcini and Angeletti, 1966, Pharmacol. Rev. 18:619–628). Exposure to NGF antibodies even earlier in development either by antibody injections in utero or by passive transplacental transfer of maternal antibodies has been shown to result in a substantial loss of neural crest-derived sensory neurons such as spinal and dorsomedial trigeminal sensory neurons (Goedert et al., 1984, Proc. Natl. Acad. Sci. U.S.A. 81:1580–1584; Gorin and Johnson, 1979, Proc. Natl. Acad. Sci. U.S.A. 76:5382–5386). Until recently, almost all studies of NGF had focused on its role in the peripheral nervous system, but it now appears that NGF also influences the development and maintenance of specific populations of neurons in the central nervous system (Thoenen et al., 1987, Rev. Physiol. Biochem. Pharmacol. 109:145–178; Whittemore and Seiger, 1987, Brain Res. Rev. 12:439–464).

The abundance of NGF protein in mouse submaxillary gland allowed the primary sequence to be determined by relatively conventional protein chemistry (Angeletti and Bradshaw, 1971, Proc. Natl. Acad. Sci. 68:2417–2420). The NGF gene has now been cloned from many species, including mouse (Scott et al., 1983, Nature 302:538–540, human (Ullrich et al., 1983, Nature 303;821–825), cow and chick (Meier et al., 1986, EMBO J. 5:1489–1493), and rat (Whittemore et al., 1988, J. Neurosci. Res., 20:402–410) using essentially conventional molecular biology based on the availability of the protein sequence of mouse NGF to design suitable oligonucleotide probes. The availability of abundant NGF has also greatly facilitated studies on the NGF receptor, which have ultimately led to the molecular cloning of one component of the NGF receptor from human and rat (Johnson et al., 1986, Cell, 47:545–554; Radeke et al., 1987, Nature 325:593–597).

It is now well established that NGF is not a ubiquitous neurotrophic factor. Within the peripheral nervous system, NGF appears not to be a survival factor for parasympathetic neurons, neural placode-derived sensory neurons or enteric neurons, as determined both from studies in vitro and in vivo. Furthermore, NGF does not appear to be a survival factor for developing motorneurons (Oppenheim, 1982, J. Comp. Neurol. 210:174–189), although these neurons do appear to express at least a low affinity form of the NGF receptor during development (Raivich et al., 1985, EMBO J. 4:637–644). The lack of effects of NGF on these neuronal types has prompted the search for other neurotrophic factors, especially factors that would sustain the survival of spinal cord motorneurons and/or parasympathetic neurons of the ciliary ganglion.

2.2.2. BRAIN-DERIVED NEUROTROPHIC FACTOR

A neurotrophic activity capable of sustaining the survival of embryonic chick dorsal root ganglion neurons in vitro was identified in the "conditioned medium" in which rat C-6 glioma cells had been cultured (Barde et al., 1978, Nature 274:818). The activity was not neutralized by antibodies to mouse NGF, suggesting the presence of another neurotrophic factor in the conditioned medium. Similar activities that could not be blocked by NGF antibodies were subsequently reported in cultures of normal adult rat brain astroglial cells (Lindsay, 1979, Nature 282:80–82; Lindsay et al., 1982, Brain Res. 243:329–343) and in extracts of developing and adult rat brain (Barde et al., 1980, Proc. Natl. Acad. Sci. U.S.A. 77:1199–1203) and developing and mature chick spinal cord (Lindsay and Peters, 1984, Neurosci. 12:45–51). However, in no case was the active factor(s) isolated or identified, and it remains questionable as to whether the observed activities were due to the same or different factor(s).

Using pig brain as a starting material, Barde et al. (1982, EMBO J. 1:549–553) reported a factor, now termed brain-derived neurotrophic factor (BDNF), which appeared to promote the survival of dorsal root ganglion neurons from E10/E11 chick embryos. The neurotrophic activity was found to reside in a highly basic protein (isoelectric point, pI 10.1) which migrated during sodium dodecyl sulfate (SDS) gel electrophoresis as a single band of 12.3 kD molecular weight. It was noted that the highly basic nature and molecular size of BDNF were very similar to the NGF monomer.

The cloning of the BDNF gene was first performed as described in U.S. patent application Ser. No. 07/400,591, filed Aug. 30, 1989, which is incorporated by reference in its entirety herein. Briefly, minute quantities of BDNF protein were purified from pig brain, allowing the determination of fragments of amino acid sequence which could, in turn, be used to design corresponding oligonucleotides. These synthetic oligonucleotides were then used as primers in polymerase chain reaction (PCR) with cDNA template prepared from BDNF producing cells. The products of PCR were utilized as probes to permit cloning of complete cDNA and/or genomic BDNF genes from a variety of species, including human, pig, rat, and mouse and the sequences of these genes were determined. Expression of recombinant BDNF was achieved in COS cells.

The first demonstration of neuronal specificity of BDNF distinct from that of NGF was the demonstration in vitro that purified BDNF supports the survival of 40–50% of sensory neurons dissociated from the neural placode-derived nodose ganglion of the chick embryo at E6, E9 or E12 (Lindsay et al., 1985, J. Cell. Sci. Supp. 3:115–129). NGF was without apparent effect on these neurons either by itself or in conjunction with BDNF. It was later shown in explant culture studies that BDNF appeared to support survival and neurite outgrowth from other neural placode-derived sensory ganglia, including the petrosal, geniculate and ventrolateral trigeminal ganglia (Davies et al., 1986, J. Neurosci. 6:1897–1904), none of which have been found to be sensitive to NGF. In all of the above studies, neutralizing antibodies to NGF had no effect upon the observed activity of BDNF. In addition to its effects on cultured neurons from peripheral ganglia, BDNF was found to stimulate survival and neuronal differentiation of cells cultured from quail neural crest (Kalcheim and Gendreau, 1988, Develop. Brain Res. 41:79–86).

Two recent studies with BDNF (Kalcheim, et al., 1987, EMBO J. 1:2871–2873; Hofer and Barde, 1988, Nature 331:261–262) have, however, indicated a physiological role of BDNF in avian PNS development. If a mechanical barrier was placed in ovo at E3/E4 (embryonic day 3 or 4) between developing dorsal root ganglia (DRG) and their CNS target in the neural tube, many DRG neurons were observed to die (Kalcheim and Le Dourarin, 1986, Develop. Biol. 116:451–46). It was postulated that this neuronal death may have been due to deprivation from a CNS (neural tube) derived neurotrophic factor. It was subsequently observed that BDNF attached to a laminin-coated sialastic membrane could prevent this cell death (Kalcheim et al., 1987, EMBO J. 1:2871–2873). Injections of BDNF into developing quail eggs has been found to reduce naturally occurring cell death in the nodose ganglion, an effect not seen with NGF (Hofer and Barde, 1988, Nature 331:261–262). In addition to its effect on peripheral sensory neurons of both neural crest and neural placode origin, BDNF was found to support the survival of developing CNS neurons. Johnson et al. (1986, J. Neurosci. 6:3031–3938) presented data indicating that BDNF supports the survival of retinal ganglion cells cultured from E17 rat embryos. This extended previous studies which showed that conditioned media and brain extracts prepared from the target regions of retinal ganglion cells appeared to support the survival of these neurons (McCaffery et al., 1982, Ex. Brain Res. 48:37–386; Sarthy et al., 1983, J. Neurosci. 3:2532–2544; Turner et al., 1983, Dev. Brain Res. 6:77–83).

In addition to its effects on the survival of developing neurons in culture, BDNF has been shown to have effects on cultured adult peripheral and central nervous system neurons. BDNF, as well as NGF, has been shown to stimulate axonal regeneration from adult rat DRG neurons in culture (Lindsay, 1988, J. Neurosci. 1:2394–2405) although adult sensory neurons did not appear to require neurotrophic factors for maintenance in vitro over 3 or 4 weeks. Furthermore, in cultures of adult rat retina, BDNF was observed to promote both survival and axonal elongation from retinal ganglion cells (Thanos et al., 1989, Eur. J. Neurosci. 1:19–26). In addition BDNF has been shown to prolong the survival of cells in ventral mesencephalic cultures, as measured by the number of tyrosine hydroxylase positive cells visualized by immunocytochemistry. In addition, BDNF enhances the survival of cholinergic neurons in dissociated cell culture derived from the rat septal region (U.S. patent application Ser. No. 07/400,591, filed Aug. 30, 1989). A comparison of the biological effects of NGF and BDNF is presented in Table I.

TABLE I

COMPARISON OF BIOLOGICAL ACTIVITIES OF BDNF AND NGF*

| | SURVIVAL** | |
|---|---|---|
| | BDNF | NGF |
| PERIPHERAL NERVOUS SYSTEM | | |
| (i) E6 Chick DRG | – | ++ |
| E10 Chick DRG | + | ++ |
| E12 Chick Symp | – | ++ |
| (Barde et al., 1980 supra) | | |
| (ii) E6 - E12 Chick DRG | ++ | ++ |
| E6 - E12 Chick Nodose | ++ | |
| E12 - Chick Sympathetic | – | ++ |
| E12 - Chick ciliary | | |
| (Lindsay et al., 1985, supra) | | |
| (iii) E3 - E14 Chick: | | |
| Jugular | +/++ | ++ |
| DM-trigeminal | +/++ | ++ |
| Petrosal | +/++ | – |
| Geniculate | +/++ | – |
| VL-trigeminal | ++ | – |
| Vestibular | – | – |
| Mesencephalic trigeminal | ++ | – |
| (Davies et al., 1986, supra) | | |
| (Barde et al., 1987, Prog. | | |
| Brain Res., 71:185-189) | | |
| CENTRAL NERVOUS SYSTEM | | |
| (i) E17 Rat Retinal Ganglion Cells | ++ | – |
| (Johnson et al., 1986, | | |
| J. Neurosci. 63031-3038) | | |
| (ii) Ventral Mesencephalon Dopaminergic Neurons | ++ | – |
| (iii) basal forebrain cholinergic neurons (U.S. Patent Application Serial No. 07/400,591, filed August 30, 1989) | ++ | ++ |

*in chronological order according to publication date; effects tested in vitro
**no surival: (–); moderate survival (+); good survival (++)

Analysis of the predicted primary structure of mature BDNF has revealed a striking similarity to NGF; with only three gaps introduced into the NGF sequences to optimize matching, 51 identities are common to the various NGFs (from snake to man) and BDNF. Importantly, these identities include six cysteine residues.

2.2.3. NEUROTROPHIN-3

The marked similarities between NGF and BDNF suggested that both may be members of a larger family of closely related neurotrophic molecules. When regions of homology were used to devise oligonucleotide primers for polymerase chain reaction to identify new members of the BDNF/NGF gene family, another member of the family, termed neurotrophin-3, was discovered and the NT-3 gene was cloned from mouse, rat, and human (see U.S. patent application Ser. No. 07/490,004, filed Mar. 7, 1990, incorporated by reference in its entirety herein). The overall structure of mature mouse NT-3 protein, consisting of 119 amino acids with a computed pI of about 9.5, was found to resemble that established for NGF and BDNF; a putative signal sequence of 18 amino acids (showing 5 and 9 amino acid identities with BDNF and NGF, respectively) appears to be followed by a prosequence of 121 amino acids (as compared with a prosequence of 103 amino acids in mouse NGF and a prosequence of 112 amino acids in mouse BDNF). A comparison between mature mouse NGF, BDNF, and NT-3 revealed 54 amino acid identities (FIG. 1). All 6 cysteine residues, known in NGF and BDNF to be involved in the formation of disulfide bridges (Leibrock et al., 1989, Nature 341:149–152;Angeletti, 1973, Biochem. 12:100–115) are amongst the conserved residues. Similarly, mature rat NT-3 appears to share 57% amino acid homology with rat NGF, and 58% amino acid homology with rat BDNF; 57 of the 120 residues (48%) appear to be shared by all three proteins (FIG. 1D). Again, the six cysteine residues of rat NGF and BDNF were found to be absolutely conserved in rat NT-3, and regions of greatest homology between the three proteins appear to cluster around these cysteine residues.

In addition to the homology between NT-3, NGF, and BDNF within a species, a high degree of conservation in nucleic acid sequence was observed between rat and human NT-3 within the region encoding the mature polypeptide (119 amino acids). The human and rat genes were found to be approximately 92% homologous in DNA sequence. However, none of the differences in nucleotide sequences between human and rat in this region lead to amino acid substitutions; the deduced amino acid sequences of mature rat and human (as well as mouse NT-3) appear absolutely identical, reminiscent of the high degree of conservation of BDNF, which shows complete identity in the amino acid sequence of the mature polypeptide among rat, mouse, human, and pig. By contrast, the amino acid sequences of mature human NGF and rodent NGF (mouse or rat) differ by approximately 10 percent.

Studies of the neurotrophic activity of NT-3 have indicated that NT-3 is capable of promoting survival and neurite outgrowth of dissociated dorsal root ganglion neurons in culture. Furthermore, NT-3 was observed to promote neurite outgrowth from both nodose ganglion and sympathetic ganglion explants, whereas BDNF promoted outgrowth from nodose ganglion but not sympathetic ganglion, and NGF promoted outgrowth from sympathetic ganglion but not nodose ganglion explants. Therefore, NT-3 appears to have a broader specificity of action than either BDNF or NGF.

NT-3 may be important in the development of the nervous system. When the relative abundance of NGF, BDNF, and NT-3 transcripts in the brains of newborn and adult mice were compared, the level of NT-3 in newborn brain was found to be higher than in adult brain. NT-3 RNA levels in the central nervous system were observed to be dramatically higher during fetal development and were found to subsequently decrease to adult levels.

2.2.4. CILIARY NEUROTROPHIC FACTOR

Ciliary neurotrophic factors (CNTFs) are proteins that specifically promote the survival of embryonic chick ciliary ganglion neurons in vitro (Manthorpe et al., 1980, J. Neurochem. 34:69–75). The ciliary ganglion is anatomically located within the orbital cavity, lying between the lateral rectus and the sheath of the optic nerve; it receives parasympathetic nerve fibers from the oculomotor nerve which innervate the ciliary muscle and sphincter pupillae.

Ciliary ganglion neurons have been found to be among the neuronal populations which exhibit defined periods of cell death. In the chick ciliary ganglion, half of the neurons present at embryonic day 8 (E8) have been observed to die before E14 (Landmesser and Pilar, 1974, J. Physiol. 241: 737–749). During this same time period, ciliary ganglion neurons are forming connections with their target tissues, namely, the ciliary body and the choroid coat of the eye. Landmesser and Pilar (1974, J. Physiol. 241:751–736) observed that removal of an eye prior to the period of cell death results in the complete loss of ciliary ganglion neurons in the ipsilateral ganglion. Conversely, Narayanan and Narayanan (1978, J. Embryol. Ex. Morphol. 44:53–70) observed that, by implanting an additional eye primordium and thereby increasing the amount of available target tissue, ciliary ganglion neuronal cell death may be decreased. These results are consistent with the existence of a neurotrophic factor which acts upon ciliary ganglion neurons.

In culture, ciliary ganglion (CG) neurons have been found to require a factor or factors for survival. Ciliary neurotrophic factor(s) (CNTF) activity has been identified in chick muscle cell conditioned media (Helfand et al., 1976, Dev. Biol. 50:541–547; Helfand et al., 1978, Exp. Cell Es. 113:39–45; Bennett and Nurcombe, 1979, Brain Res. 173:543–548; Nishi and Berg, 1979, Nature 277:232–234; Varon et al., 1979, Brain Res. 173:29–45), in muscle extracts (McLennan and Hendry, 1978, Neurosci. Lett. 10:269–273; Bonahandy et al., 1980, Neurosci. Lett. 18:197–201), in chick embryo extract (Varon et al., 1979, Brain Res. 173:29–45; Tuttle et al., 1980, Brain Res. 183:161–180), and in medium conditioned by heart cells (for discussion, see also Adler et al., 1979, Science 204:1434–1436 and Barbin et al., 1984, J. Neurochem. 43:1468–1478).

CNTF has been purified from rat sciatic nerve and the amino acid sequence of various fragments determined by gas phase microsequencing; the resulting amino acid sequence was used to clone a rat CNTF gene using polymerase chain reaction-based cloning techniques (U.S. patent application Ser. No. 07/408,172, filed Sep. 15, 1989, and U.S. patent application Ser. No. 07/429,517, filed Oct. 31, 1989 which are incorporated herein by reference in its entirety). A rat CNTF probe were subsequently used in the cloning of the human CNTF gene. Comparison of the nucleic acid sequences of human and rat CNTF genes indicate that the human gene has a single intron at the same position as the rat CNTF gene. Within the intron, the human sequences appear to have diverged considerably from the rat, in marked contrast to substantial conservation of the coding region.

Based on nucleotide sequence, CNTF may be predicted to have a molecular weight of about 22.8 KD (calculated from an estimated size of about 200 amino acids), which is in agreement with that estimated for naturally occurring CNTF from polyacrylamide gel electrophoresis analysis (22.5 KD; Saadat et al., 1989, J. Cell Biol. 108:1807–1816). Thus, the amino acid sequence of CNTF shows the features of a cytosolic protein, i.e. no signal peptide, no consensus sequences for glycosylation and only one cysteine residue at position 17. No sequence homology was observed between CNTF and NGF, BDNF, or fibroblast growth factor (FGF) and purpurin, each of which are associated with survival activities similar to those of CNTF (Unsicker et al., 1987, Proc. Natl. Acad. Sci. U.S.A., 84:5459–5463; Schubert et al., 1986, J. Cell Biol. 102:2295–2301)

A number of biological effects have been ascribed to CNTF. CNTF was originally described as an activity which supported the survival of neurons of the E8 chick ciliary ganglion, which is a component of the parasympathetic nervous system. Saadat et al., (1989, J. Cell Biol. 108:1807–1816) observed that their most highly purified preparation of rat sciatic nerve CNTF induced cholinergic differentiation of rat sympathetic neurons in culture. Also, Hoffman (1988, J. Neurochem. 51:109–113) found that CNTF activity derived from chick eye increased the level of choline-O-acetyltransferase activity in retinal monolayer cultures.

Hughes et al. (1988, Nature 335:70–73) studied a population of bipotential glial progenitor cells in the perinatal rat optic nerve and brain; this cell population is believed to give rise to, first, oligodendrocytes and then, second, to type 2 astrocytes. Studies have suggested that oligodendrocyte differentiation occurs from an oligodendrocyte-type 2-astrocyte (0-2A) progenitor cell in the absence of any particular growth factor, whereas type 2 astrocyte differentiation appears to require the presence of a specific inducing protein. Hughes et al. observed that the type 2 astrocyte inducing protein is similar or identical to CNTF (see also Anderson, 1989, Trends Neurosci. 12:83–85).

In addition, recombinant CNTF has been shown to promote the survival of mediodorsal spinal cord neurons in culture, and purified rat sciatic nerve CNTF was observed to prevent lesion-induced cell death of motorneurons in lesioned facial nerve of newborn rat (U.S. patent application Ser. No. 07/429,517, filed Oct. 31, 1989, incorporated herein by reference in its entirety).

Table II outlines a list of activities associated with NGF, BDNF, NT-3, and CNTF; additional activities, as yet unidentified, are likely to be documented.

TABLE II

CELLS RESPONSIVE TO NEUROTROPHIC FACTORS

I. Cells Responsive to NGF

| | |
|---|---|
| A. | Sympathetic neurons |
| B. | Neural Crest-derived sensory neurons |
| C. | E6-E12 dorsal root ganglia |
| D. | Basal Forebrain Cholinergic Neurons |

II. Cells Responsive to BDNF

| | |
|---|---|
| A. | Sensory neurons of neural crest origin |
| | (i) dorsal root ganglion (E10/E11) |
| | (ii) jugular ganglion |
| | (iii) dorsomedial trigeminal ganglion |
| | (iv) trigeminal mesencephalic nucleus |
| B. | Sensory neurons of ectodermal placode origin |
| | (i) nodose ganglion |
| | (ii) vestibular ganglion |
| | (iii) petrosal ganglion |
| | (iv) geniculate ganglion |
| | (v) ventrolateral trigeminal ganglion |
| C. | Retinal ganglion |

TABLE II-continued

CELLS RESPONSIVE TO NEUROTROPHIC FACTORS

| | |
|---|---|
| D. | Ventral mesencephalic dopaminergic neurons |
| E. | Basal forebrain cholinergic neurons |

III. Cells responsive to NT-3

| | |
|---|---|
| A. | Dorsal root ganglion |
| B. | Sympathetic ganglion |
| C. | Nodose ganglion |

IV. Cells responsive to CNTF

| | |
|---|---|
| A. | E8 ciliary ganglion |
| B. | Sympathetic cholinergic neurons |
| C. | Type 2 astrocytes |
| D. | Mediodorsal spinal cord neurons |
| E. | Motorneurons (e.g. facial nerve motorneurons) |
| F. | E10 DRG Neurons |

3. SUMMARY OF THE INVENTION

The present invention relates to chimeric neurotrophic factors which comprise at least a portion of a naturally occurring cellular factor and a portion of at least one other molecule such that the resulting chimeric molecule has neurotrophic activity. It is based, in part, on the discovery that chimeric molecules comprising portions of both NGF and BDNF are likely to possess neurotrotrophic activity, and in some cases exhibit a spectrum of activity larger than that of either parent molecule. It is further based on the discovery that chimeric molecules comprising neurotrophic factor sequences as well as additional peptide sequences may retain neurotrophic activity, and in some cases may exhibit a more potent activity than the parent factor.

The present invention provides for nucleic acids encoding chimeric neurotrophic factors, for methods of expressing these chimeric neurotrophic factors, for chimeric neurotrophic factor proteins and peptide fragments and derivatives thereof, for antibodies directed toward chimeric neurotrophic factors for defining specificity determinants, and for methods of diagnosis and treatment of neurological disorders which utilize the chimeric neurotrophic factors of the invention. The present invention also provides for a number of particular recombinant plasmids which encode biologically active neurotrophins.

The chimeric neurotrophic factors of the invention provide a number of advantages relative to naturally occurring neurotrophic factors. Chimeric neurotrophic factors may provide, for example, the activity of two neurotrophic factors in a single molecule, or may serve as superagonists of an endogenous neurotrophic factor, thereby enabling an increased biological response at lower doses. Additionally the chimeric neurotrophic factors of the invention may be useful in targeting an active compound to cells responsive to neurotrophic factor. Furthermore, the design of chimeric neurotrophic factors which retain specific biological activity but which are directed to a subset of factor-responsive cells may enable the treatment of neurological disorders but avoid the complications of more widespread activity of a parental molecule(s).

4. BRIEF DESCRIPTION OF THE FIGURES

FIG. 1. Schematic diagram of the strategy utilized in the construction of BDNF-NGF chimeras using three oligonucleotide primers and single-step polymerase chain reaction. Primers were designed such that the reaction product would comprise Nar 1 and Not 1 restriction enzyme cleavage sites which would facilitate the insertion of the product after the BDNF prepro region sequence in pC8hB(P1) expression plasmid. Hatched areas represent NGF sequence, open areas represent BDNF sequence.

Figure 2:
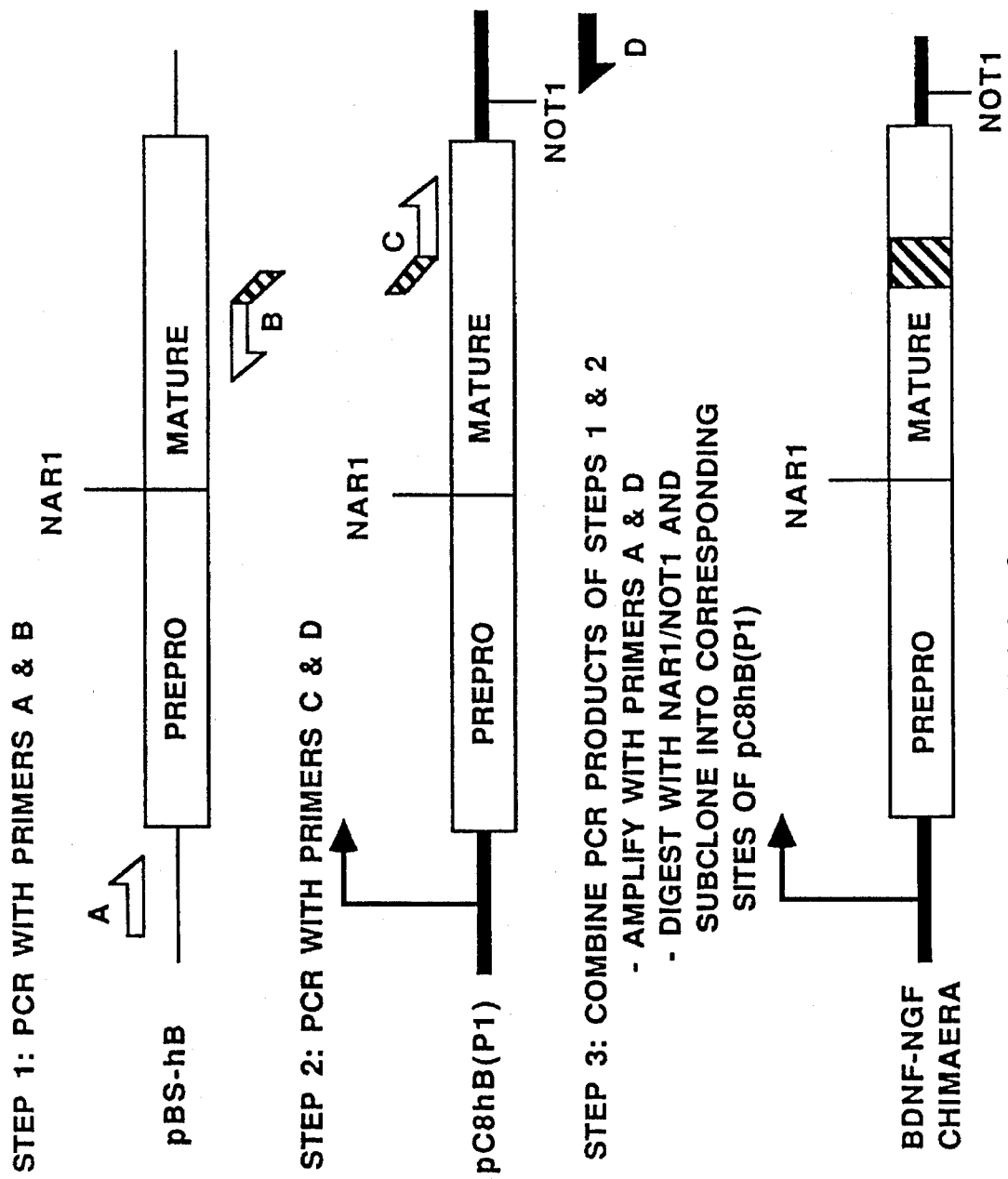

FIG. 2. Schematic diagram of the strategy utilized in the construction of BDNF-NGF chimeras using four oligonucleotide primers in a three-step polymerase chain reaction. The hatched areas represent NGF sequence, solid areas represent vector sequence, and open areas represent BDNF sequence.

Figure 3A:
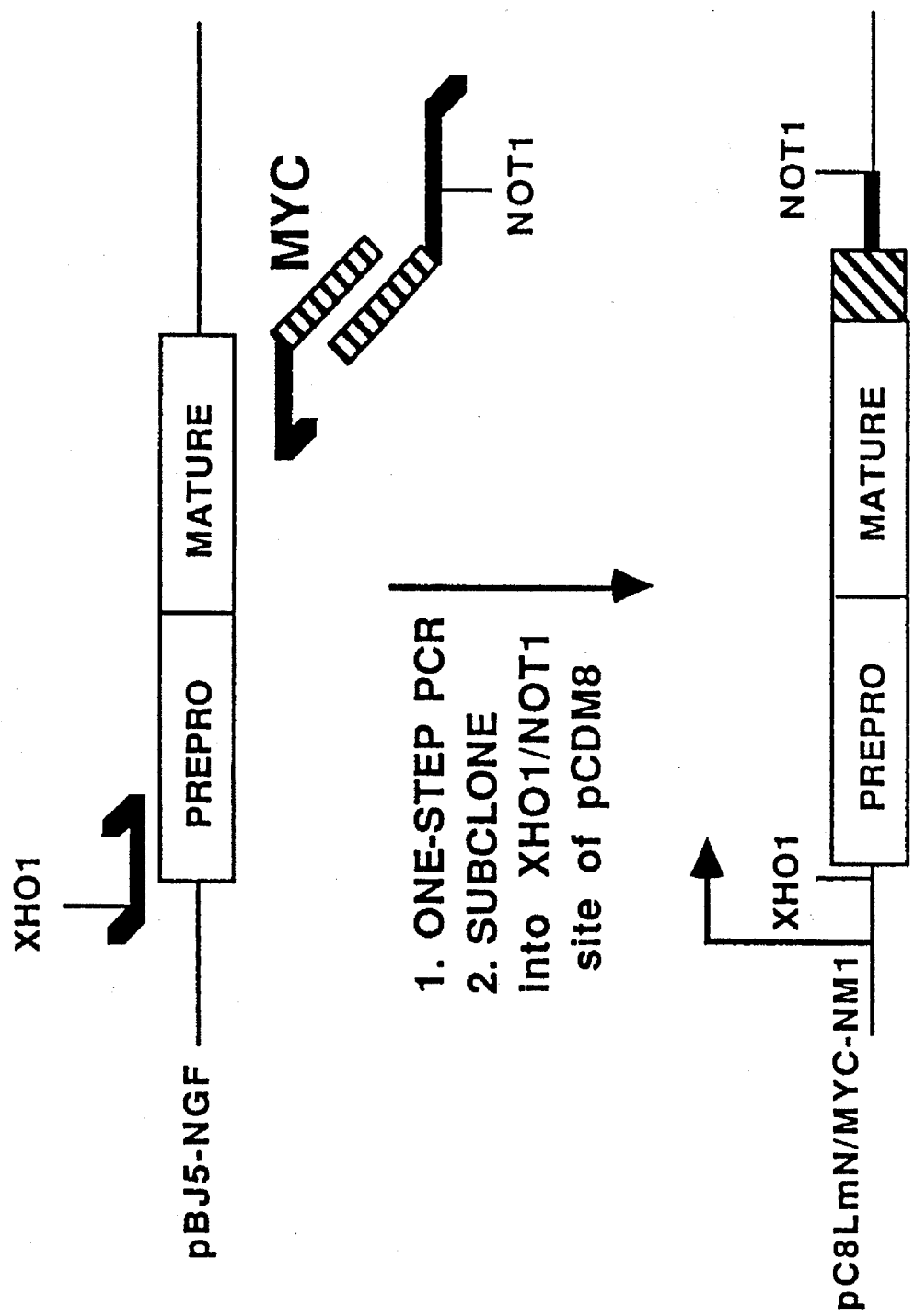
Figure 3B:
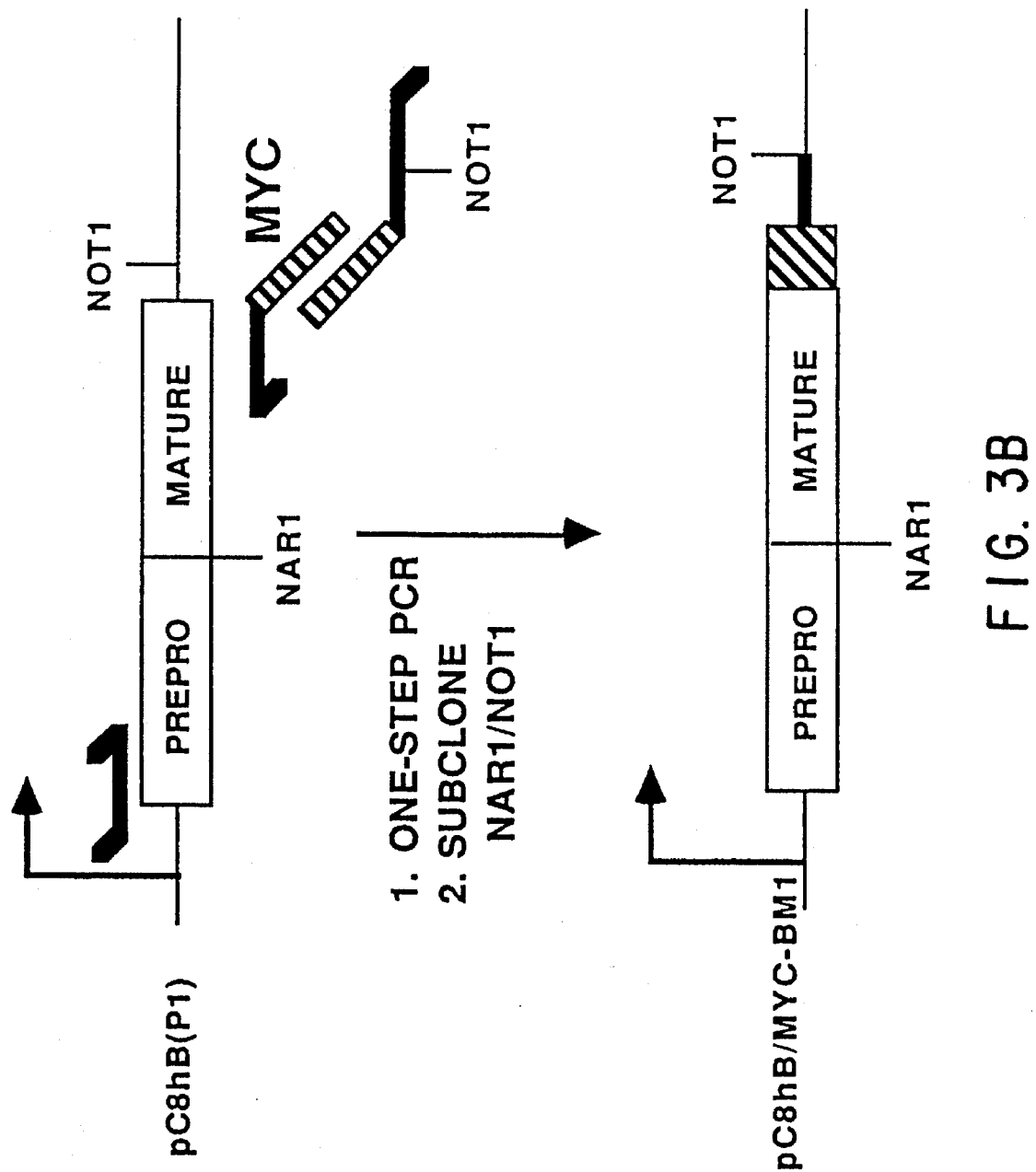

FIG. 3A–B. Schematic diagram of the strategy utilized in construction of myc-tagged neurotrophic factor chimeras.

FIG. 3A. Construction of myc-tagged NGF; myc sequences are hatched and open regions represent NGF sequence.

FIG. 3B. Construction of myc-tagged BDNF; myc sequences are hatched and open regions represent BDNF sequence.

Figure 4:
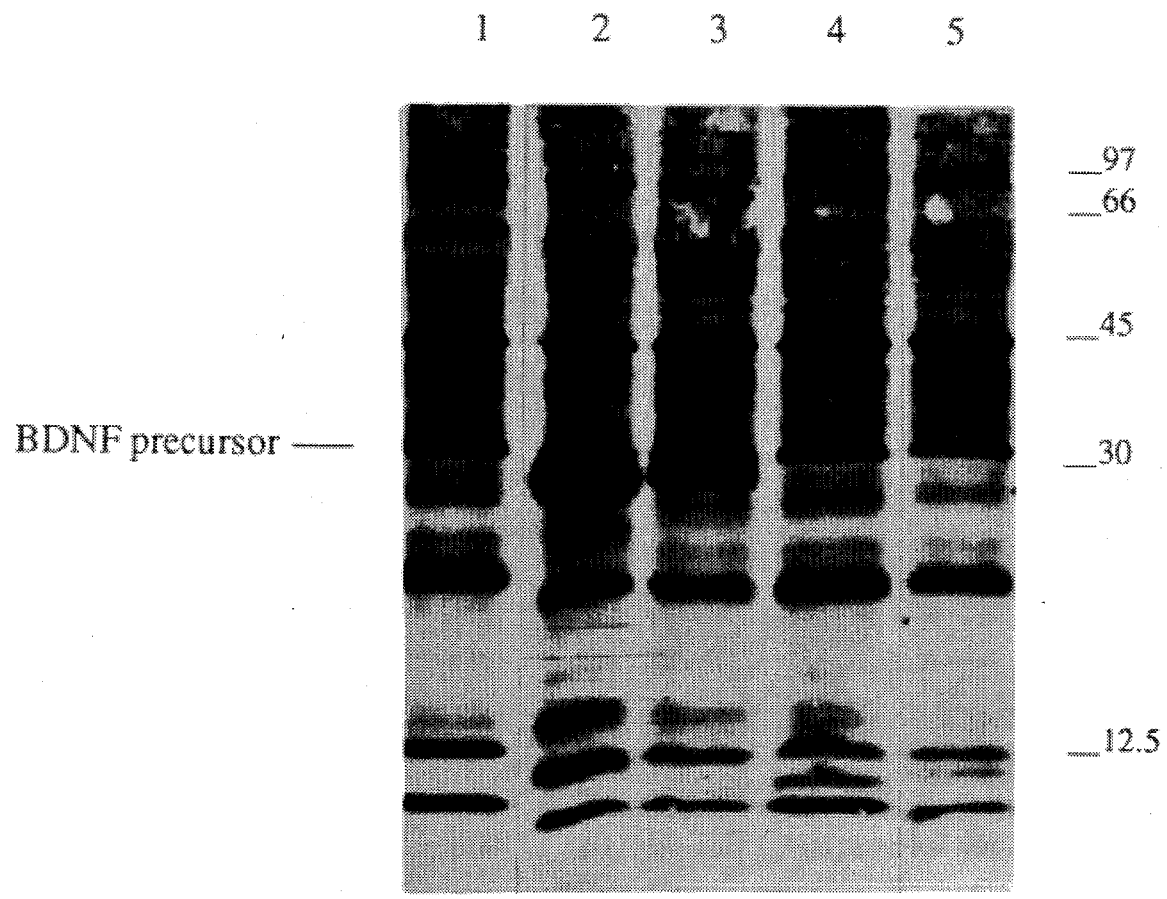

FIG. 4. 50 µl of $^{35}$S-labeled COS cell supernatant was resolved by 15% SDS PAGE and labeled proteins were elecrophoretically transferred to a nylon membrane. The membrane was exposed to film overnight and the resulting autoradiograph was photographed. Lane 1, COS MOCK; Lane 2, human BDNF; Lane 3, hBDNF/3'myc (BM1); Lane 4, mNGF; Lane 5, mNGF/3'myc (NM1). Molecular weight standards are indicted.

FIG. 5A–D. Deduced amino acid sequence of chimeric neurotrophic factors R1 through R10, BM1 and NM1.

Figure 6A:
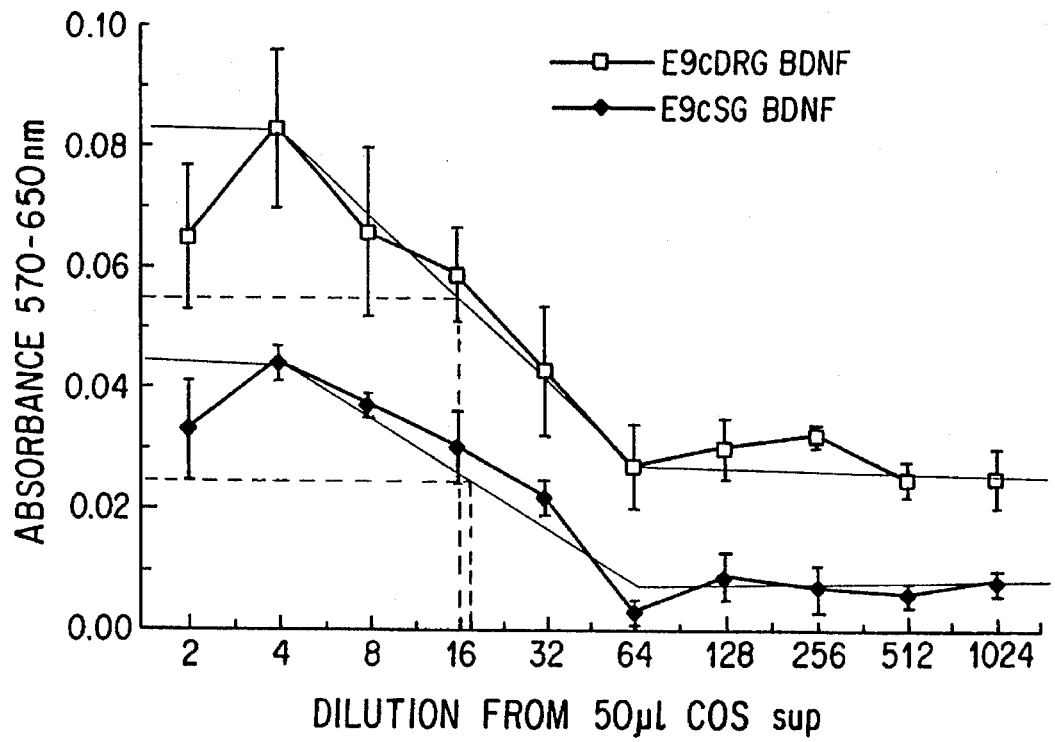
Figure 6B:
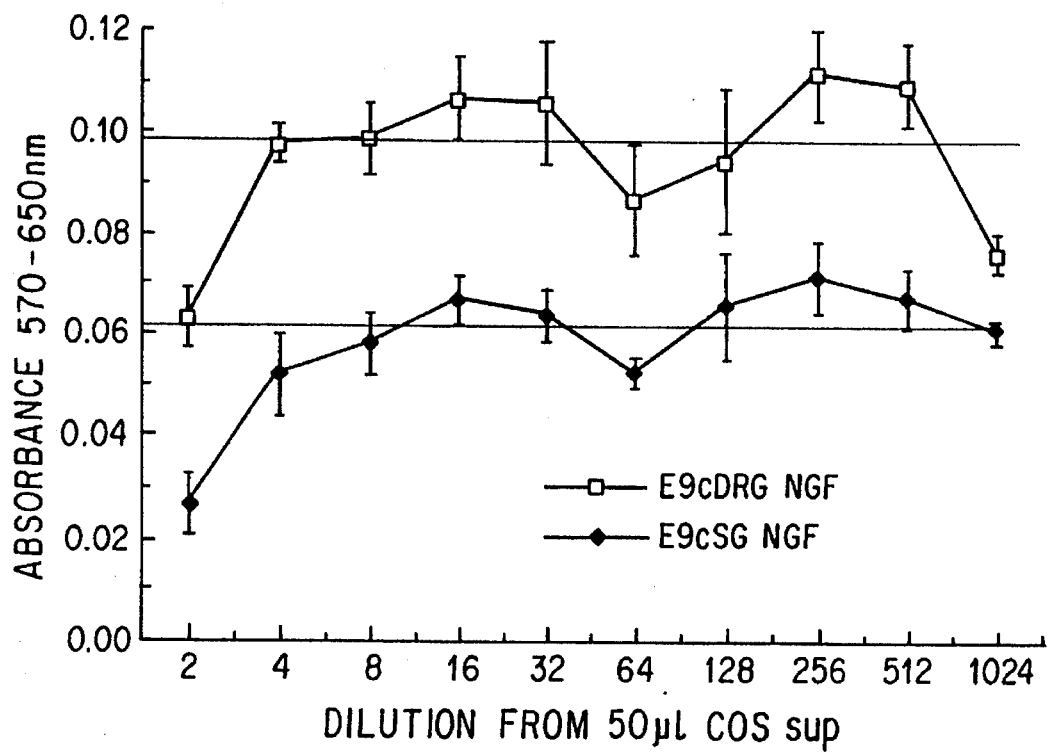
Figure 6C:
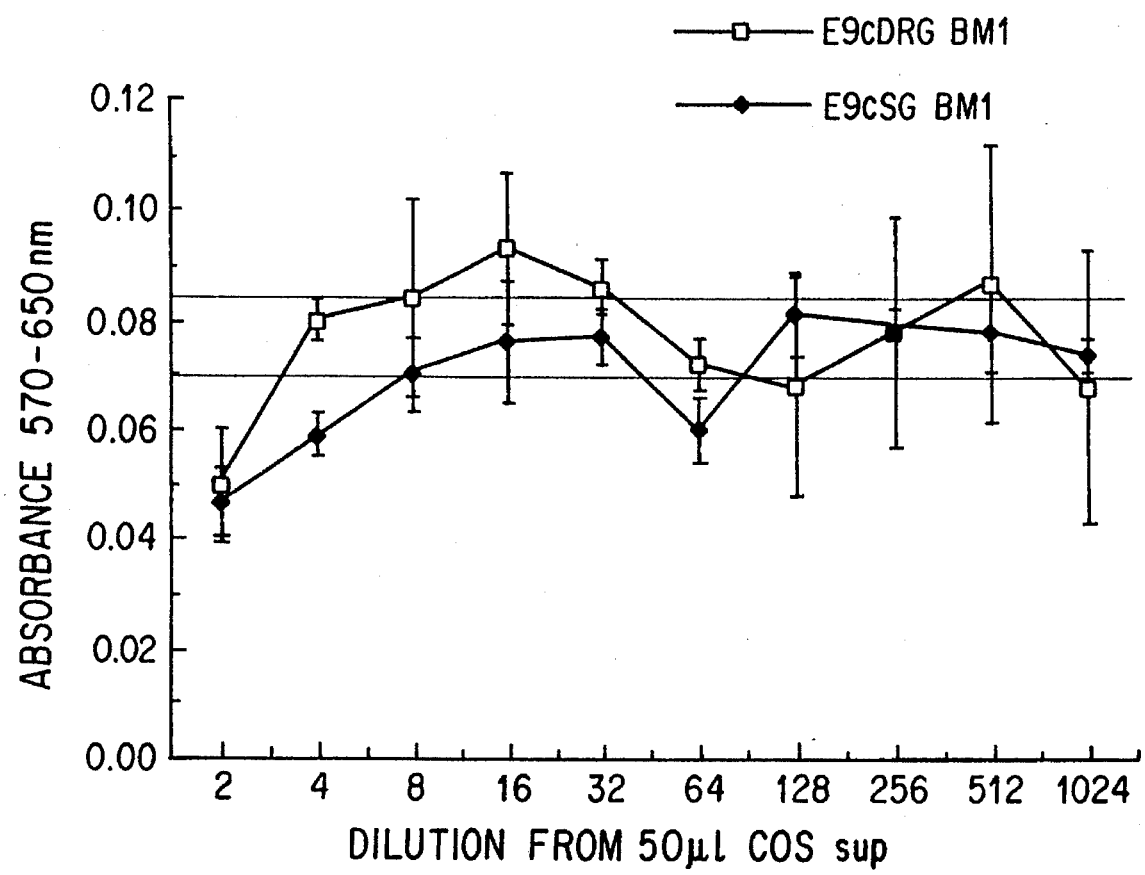

FIG. 6A–C. MTT colorimetric assay results for dorsal root ganglia (DRG) or sympathetic ganglia (SG) treated with FIG. 6A BDNF; FIG. 6B NGF or FIG. 6C BM1, myc-tagged BDNF. Absorbance at 570–650nm is plotted as a function of increasing dilution of COS cell supernatant containing neurotrophic activity.

Figure 7:
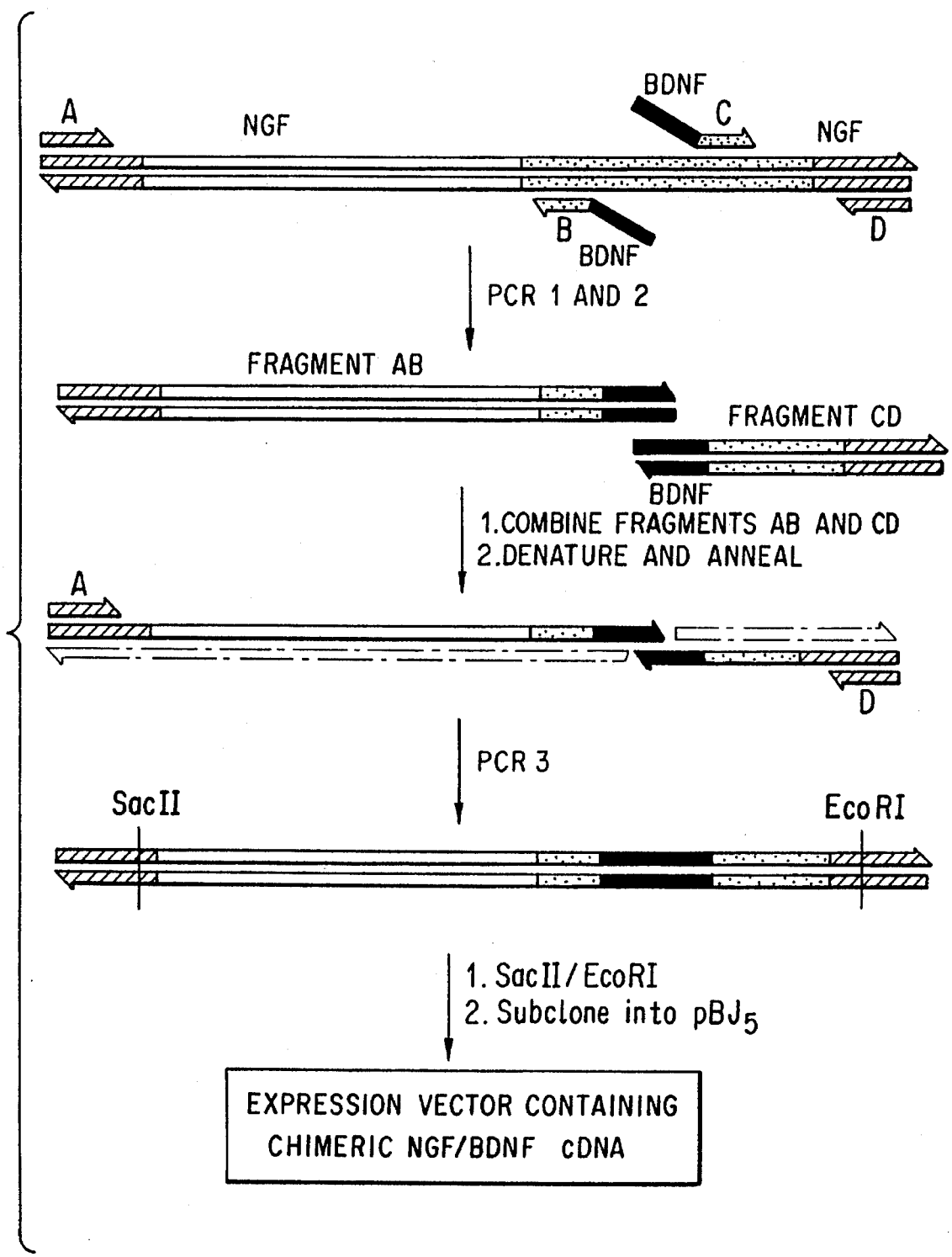

FIG. 7. Schematic diagram of the strategy utilized in the construction of NGF-BDNF Chimeras using four oligonucleotide primers in a three-step polymerase chain reaction. Primer A is the T7 primer, primers B and C differ amongst the twelve chimeras produced and are presented in Table 10, and primer D is the T3 primer. The hatched areas represent vector sequence, the open areas represent prepro sequence, the stippled areas represent mature NGF sequence and the solid areas represent BDNF sequence.

Figure 8A:
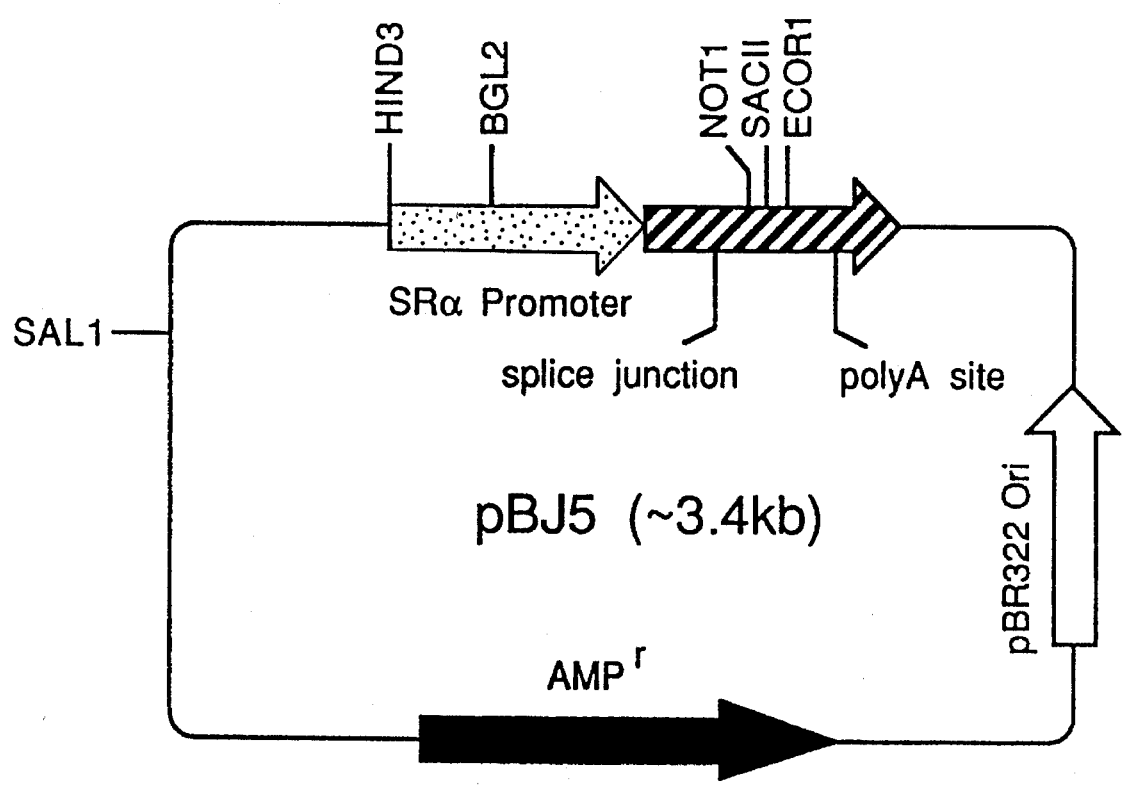

FIG. 8A. The modified PBJ-5 vector used in the expression of NGF-BDNF chimeric neurotrophic factors. The vector contains the ampicillin resistance gene (solid arrow), the pBR322 origin of replication (open arrow), the SR promoter (stippled arrow; Takebe et al., 1988, Mol. Cell. Biol. 8:466–472) and a cloning site (hatched arrow) comprising a splice junction, poly A site, and Not 1, Sac II, and Eco R1 restriction endonuclease cleavage sites.

Figure 8B:
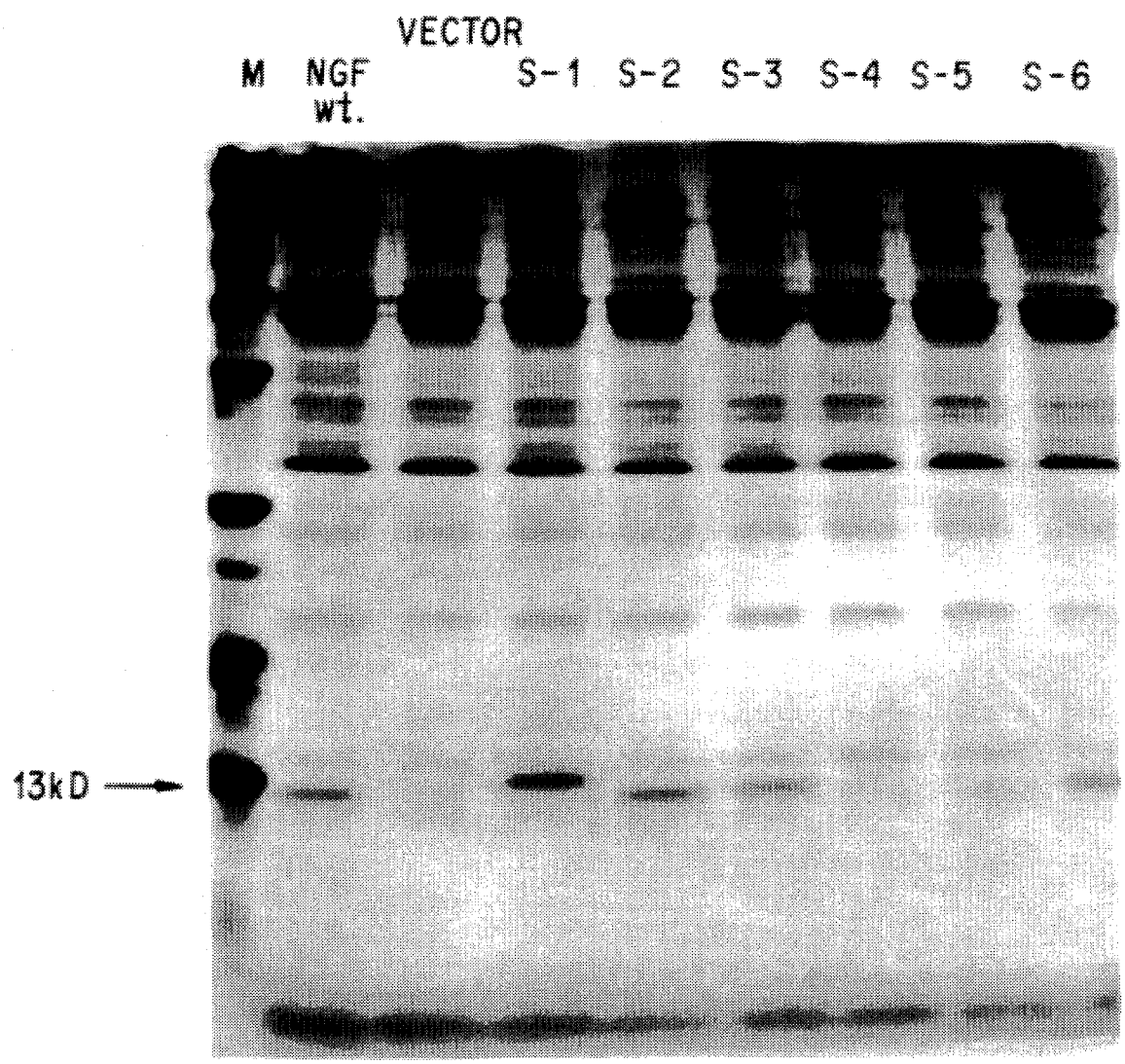
Figure 8C:
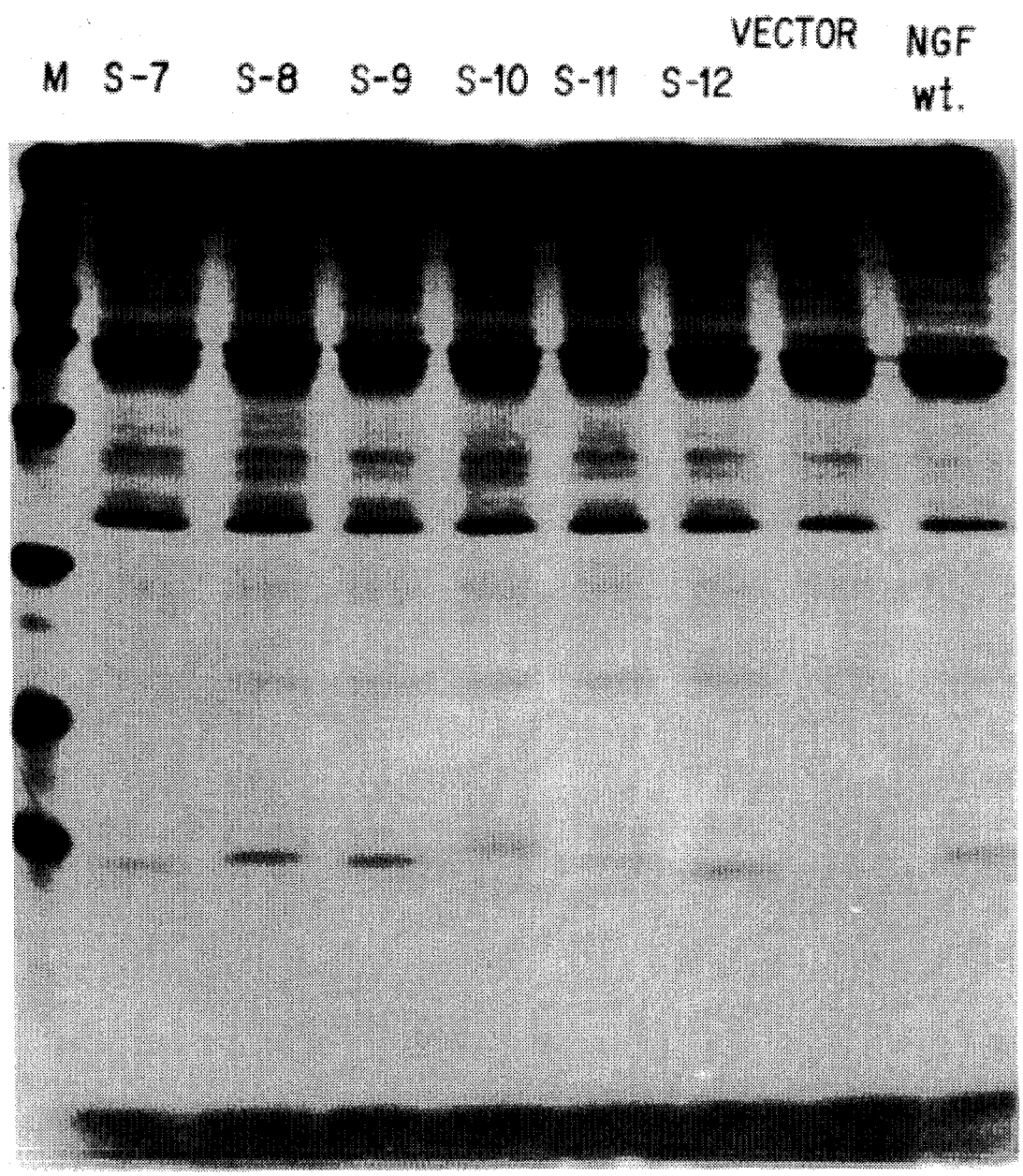

FIG. 8B and C. Results of metabolic labelling of COS cells transfected with wild-type NGF, vector (control) and NGF-BDNF chimeras S1-S12. 40 µl of COS-cell supernatant was loaded directly and electrophoresed on a 12.5 percent SDS-polyacrylamide gel.

Figure 8D:
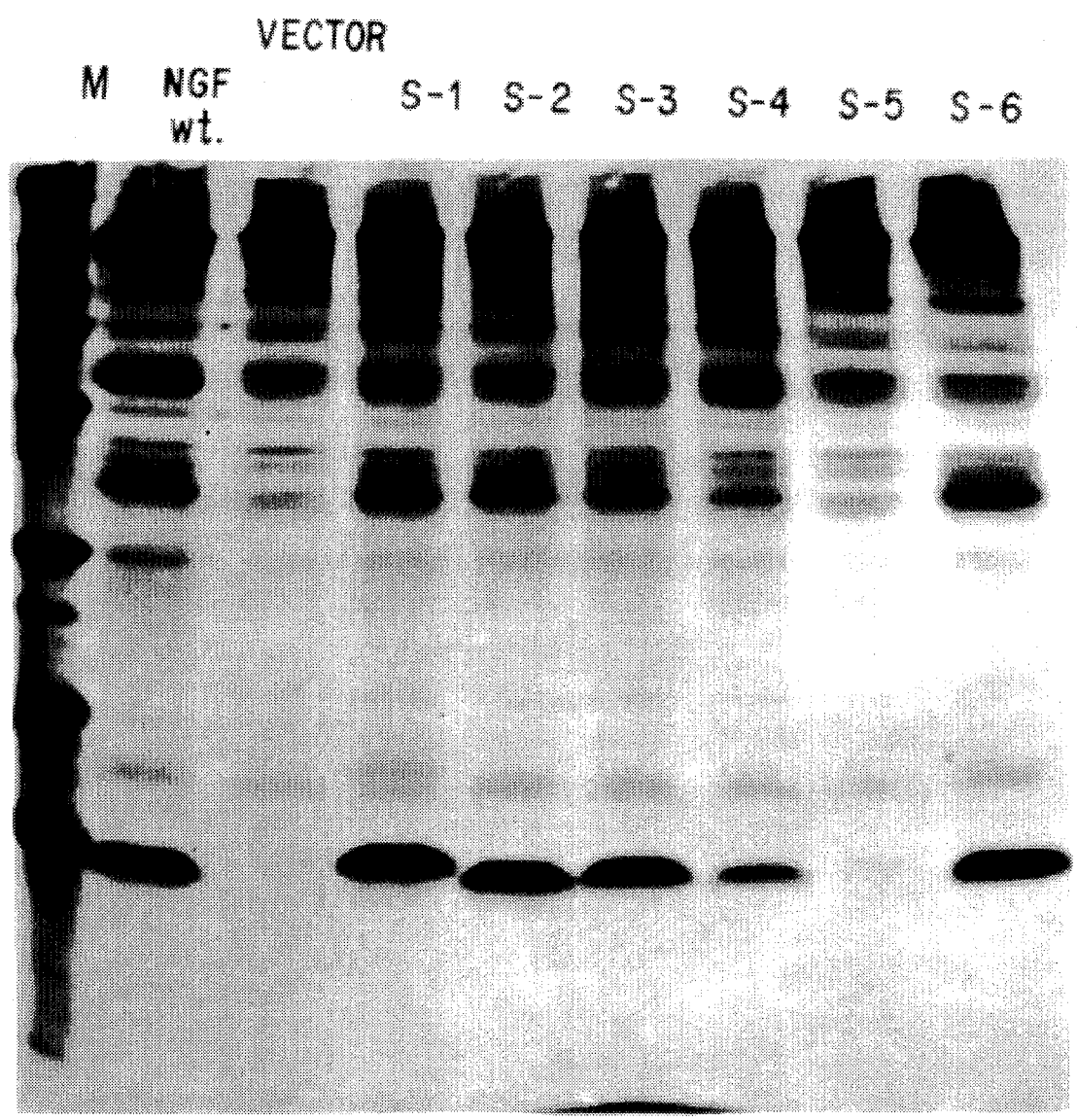
Figure 8E:
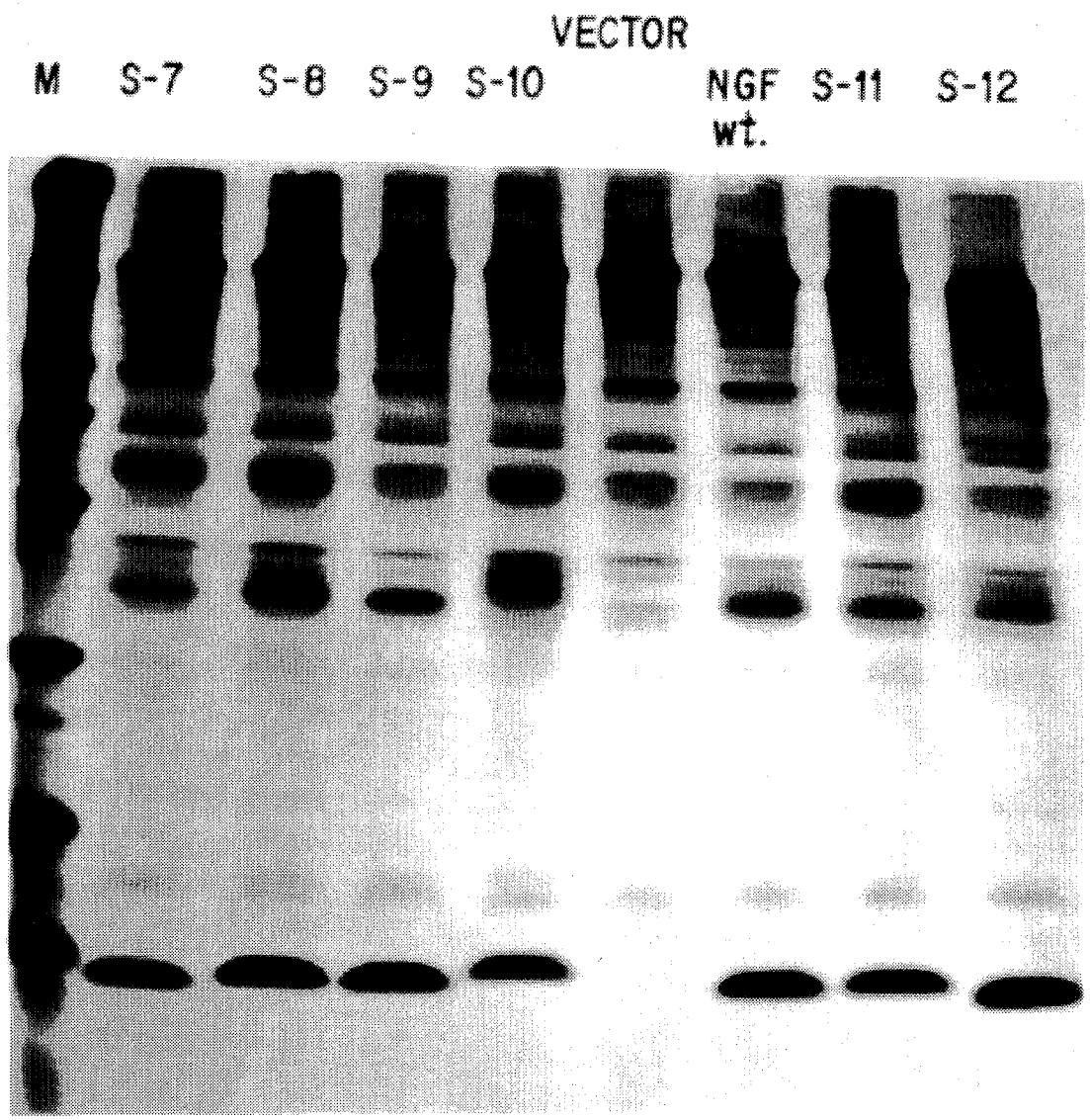

FIG 8D and E. SDS-polyacrylamide gel electrophoresis of metabolically labelled proteins in supernatants of COS cells transfected with wild-type NGF, vector (control) and NGF-BDNF chimeras S1-S12 immunoprecipitated with anti-NGF antibody. Immunoprecipitation was performed on 400 µl of supernatant. Electrophoresis was done on a 12.5 percent SDS-polyacrylamide.

Figure 9A:
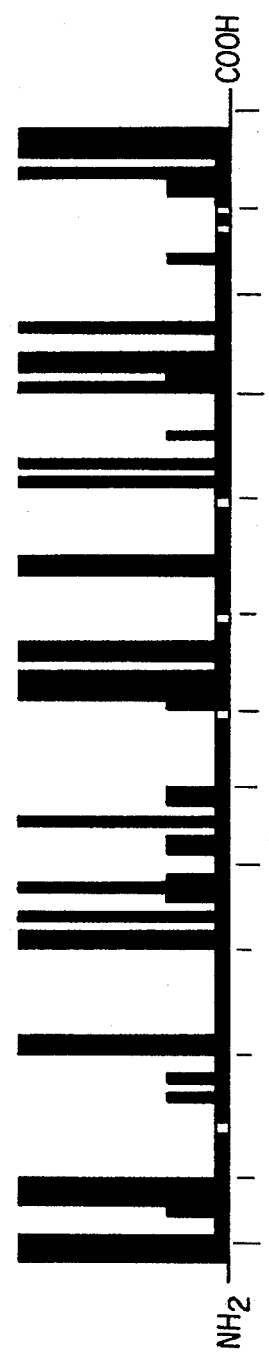

FIG. 9A. Amino-acid sequence comparison between NGF molecules isolated from different species.

Figure 9B:
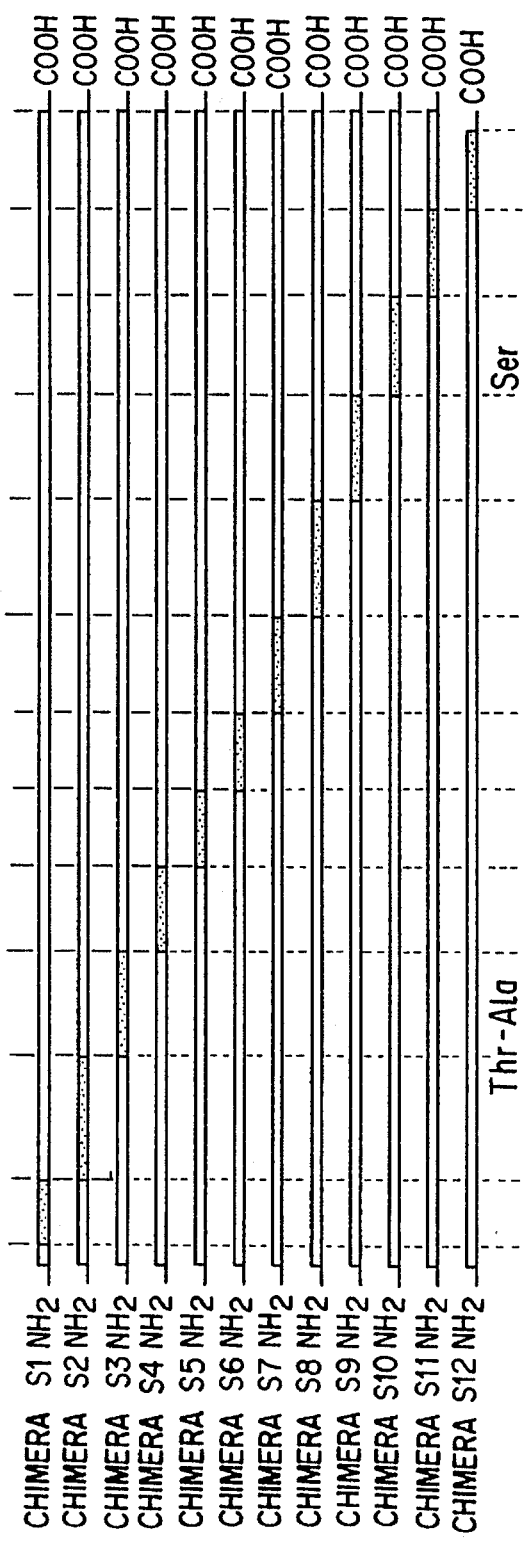

FIG. 9B. Diagram of chimeras S1-12, in which open regions represent NGF sequence and solid regions represent BDNF sequence.

Figure 9C:
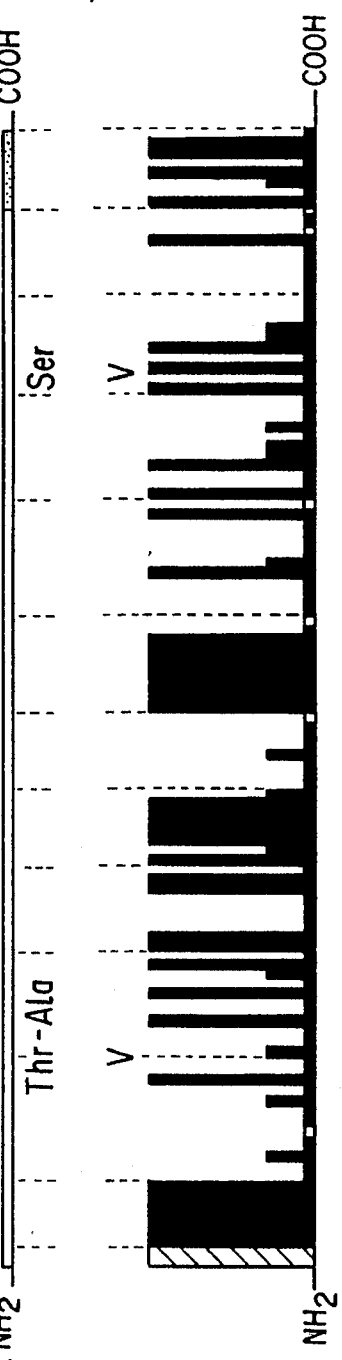

FIG. 9C. Amino-acid sequence comparison between NGF and BDNF sequences.

High Bars: Highly variable amino acids at this position allowed.

Low Bars: Only conservative amino acid changes are allowed at this position.

No Bar: Amino acids at this position are conserved throughout every known NGF and BDNF.

FIG. 10A–F. Deduced amino acid sequence of chimeric neurotrophic factors S1-12.

FIG. 11. Amino acid sequences of NGF, BDNF, and NT-3. Arrows indicate cysteine residues. Variable regions V1-V4 are indicated by overbars.

5. DETAILED DESCRIPTION OF THE INVENTION

For purposes of clarity of description, and not by way of limitation, the detailed description of the invention is divided into the following subsections:

(i) chimeric neurotrophic factors of the invention;

(ii) the construction of chimeric neurotrophic factors;

(iii) expression of chimeric neurotrophic factors;

(iv) neurotrophic factor assays for characterization of the activity and neuronal specificity of chimeric neurotrophic factors;

(v) antibodies directed toward chimeric neurotrophic factors; and (vi) utility of the invention.

5.1. CHIMERIC NEUROTROPHIC FACTORS OF THE INVENTION

The present invention provides for chimeric neurotrophic factors which (i) comprise at least a portion of a cellular factor as well as a portion of at least one other protein and (ii) have neurotrophic activity. The chimeric neurotrophic factors of the invention may comprise cellular factors, or portions thereof, which may or may not themselves possess neurotrophic activity, including, but not limited to, nerve growth factor, brain-derived growth factor, neurotrophin-3, ciliary neurotrophic factor, fibroblast growth factor (acidic or basic and related family members), epidermal growth factor, tumor growth factor beta, tumor growth factor alpha, interleukin 1, interleukin 2, alpha interferon, beta interferon, gamma interferon, growth hormone, vasoactive intestinal peptide, vasopressin, and insulin, to name but a few.

The chimeric molecules of the invention comprise at least a portion of cellular factor as well as a portion of at least one other peptide or protein, said peptide or protein which may or may not be derived from a compound which has neurotrophic activity. This peptide or protein may comprise, for example, all, or part, of a neurotrophic factor, cellular factor, toxin, enzyme, immunoglobulin, or any other peptide sequence which may or may not be associated with functional activity and may or may not be antigenic.

For example, and not by way of limitation, the present invention provides for the following chimeric molecules which exhibit neurotrophic activity as set forth in Section 5.4., infra:

(i) a chimeric molecule which comprises two complete neurotrophic factors linked together;

(ii) a chimeric molecule which comprises one complete neurotrophic factor linked to one complete non-neurotrophic cellular factor;

(iii) a chimeric molecule which comprises portions of two neurotrophic factors;

(iv) a chimeric molecule which comprises a portion of a neurotrophic factor as well as a portion of a non-neurotrophic cellular factor;

(v) a chimeric molecule which comprises at least a portion of a neurotrophic factor and a peptide sequence which may or may not be antigenic; and (vi) a chimeric molecule which comprises at least a portion of two neurotrophic factors as well as a peptide sequence which may or may not be antigenic.

The chimeric neurotrophic factors of the invention may also be linked to non-peptide compounds. For example, it may be desireable to link a carbohydrate, lipid moiety, or other organic compound to a chimeric neurotrophic factor. Such compounds would include toxic agents, antiproliferative agents, highly immunogenic agents, anticogenic agents, anti-anticogenic agents, coagulants, anticoagulants, fluorescent compounds, radioactive compounds, and the like.

Where portions of a neurotrophic factor or other cellular factor and another neurotrophic or other cellular factor are combined, it may be desireable to design the chimeric molecule such that a portion of one factor is deleted and then replaced by a portion of the other factor, thereby maintaining the approximate size of one of the parent factors, although the invention is not so limited. Furthermore, if the two factors comprise homologous regions, it is preferred that homologous regions be exchanged, one for the other, thereby creating a chimeric molecule which is homologous to, but distinct from, both parent factors. In additional embodiments, a region of a factor which is believed to have minimal function may be replaced by a region of another factor or other peptide which is believed to be biologically active; such a chimera may exhibit increased biological activity relative to the parent factors. Alternatively, a region of a factor which is believed to be associated with an undesireable biological activity may be replaced by a portion of another factor or other peptide such that the undesireable activity may be reduced or eliminated; such embodiments may be useful in the development of chimeric neurotrophic factors with minimal undesireable side effects or toxicities.

Alternatively, chimeric molecules of the invention may be encoded by nucleic acid sequence in which a sequence encoding a cell factor is interrupted by a sequence incoding a peptide or protein, such that the chimeric neurotrophic factor encoded by such a molecule is characterized by an insertion within the factor protein. Additionally, the invention provides for amino terminal as well as carboxy terminal fusions between at least a portion of a factor and another peptide.

In some instances, where homologous portions of two factors are exchanged, the chimeric molecule may effectively differ from one of its parent compounds by a single amino acid; such chimeric neurotrophic factors are contemplated by the present invention, and are exemplified by chimeras S-6 and S-11, discussed in Section 8, infra.

In preferred embodiments of the invention, chimeric neurotrophic factors are created by exchanging corresponding portions of related neurotrophic factors. In specific preferred embodiments of the invention, chimeric neurotrophic factor molecules comprise portions of two or more members of the recently identified "neurotrophin" family, including NGF, BDNF, NT-3 and any additional members as yet to be identified. According to these specific embodiments, portions of members of the neurotrophin family may be rearranged so as to preserve the secondary and/or tertiary structure of the molecule. In additional embodiments of the invention, insertion of non-neurotrophin family peptide sequences, or replacement of a portion of neurotrophin family coding sequence with a non-neurotrophin family peptide sequence, may be accomplished such that the secondary and/or tertiary structure and conformation associated with neurotrophin family members is preserved. As used herein, the phrase secondary and/or tertiary structure and conformation associated with neurotrophin family members may be construed to refer to sequence, structural, and chemical features shared by members of the neurotrophin family, namely, a length of about 120 amino acid residues, a pI between about 9 and 10, and 6 cysteine residues located approximately (within about five amino acids) at amino acids 14, 57, 67, 79, 108 and 110 or at similar positions with reference to an insertion or deletion in the homologous sequence shared by members of the neurotrophin family; for example, the fish NGF sequences carries a 22 bp insertion at adult amino acid 65 which presumably loops out so as to leave the structure of the remainder of the molecule in a conformation similar to that of mammalian NGF. In preferred specific embodiments of the invention, chimeric neurotrophic factors which comprise a portion of at least one neurotrophin family member comprise at least four cysteine residues at about the abovementioned positions. In more preferred specific embodiments, the chimeric neurotrophic factors of the invention comprise at least five cysteine residues at about the abovementioned positions. In most preferred specific embodiments of the invention, chimeric molecules comprise six cysteine residues at about the abovementioned positions. In additional preferred specific embodiments of the invention, chimeric neurotrophic factors comprise at least four cysteine residues at about the abovementioned positions and exhibit a pI of between about 9 and 10. In more preferred embodiments of the invention, chimeric neurotrophic factors comprise at least five cysteine residues at about the abovementioned positions and exhibit a pI of about 9 and 10. In most preferred specific embodiments of the invention, chimeric molecules comprise six cysteine residues at about the abovementioned positions and exhibit a pI of between about 9 and 10.

The present invention provides for nucleic acids encoding chimeric neurotrophic factors, and for chimeric neurotrophic factor proteins and peptide fragments and derivatives thereof. In preferred embodiments of the invention, a chimeric neurotrophic factor comprises a portion of at least one neurotrophin family member (see supra) including, but not limited to, NGF, BDNF, and NT-3, the sequences of which are set forth in FIG. 11. In preferred specific embodiments of the invention, chimeric neurotrophic factors have an amino acid sequence as set forth in FIGS. 5A–D and 10A–F for chimeric molecules R1 through R10, BM1, NM1, and S1 through S12. The chimeric neurotrophic factor molecules of the invention include, but are not limited to, those containing, as a primary amino acid sequence, all or part of the amino acid sequence substantially as depicted in FIGS. 5 and 10 including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are chimeric neurotrophic factor proteins or fragments or derivatives thereof which are differentially modified during or after translation, e.g., by glycosylation, proteolytic cleavage, linkage to an antibody molecule or other cellular ligand, etc. The present invention also provides for nucleic acid molecules which encode the amino acid sequences as set forth in FIGS. 5 and 10, or portions or functional equivalents therof. In addition, the present invention provides for the plasmids pBJ51mN/hB-S1 through 12, pC8hB/hN-R1 through 10, pC81mN/myc-NM1 and pC8hB/myc-BM1, set forth in Section 10, as well as the chimeric neurotrophic factor encoding nucleic acid sequences which they comprise.

The present invention provides for chimeric neurotrophic factors which comprise cellular factor derived from any living organism, including, but not limited to, human, simian, porcine, ovine, bovine, equine, canine, feline, rodent, or avian cellular factors.

5.2. THE CONSTRUCTION OF CHIMERIC NEUROTROPHIC FACTORS

Nucleic acids encoding chimeric neurotrophic factors may be constructed using standard recombinant DNA technology, for example, by cutting and splicing nucleic acid which encode cellular factors and/or other peptides using restriction enzymes and DNA ligase. Alternatively, nucleic acid sequences may be constructed using chemical synthesis, such as solid-phase phosphoramidate technology. In preferred embodiments of the invention, polymerase chain reaction (PCR; Saiki et al., 1985, Science 230:1350–1354) may be used to accomplish splicing of nucleic acid sequences by overlap extension (Horton et al., 1989, Gene 77:61–68) and thereby produce the chimeric neurotrophic factors of the invention. As discussed in detail in Section 6, infra, chimeric neurotrophic factors may be produced by a one-step PCR utilizing three oligonucleotide primers or, alternatively, by a three-step PCR utilizing four oligonucleotide primers. FIGS. 1 and 2 are schematic diagrams of these two techniques. For example, a nucleic acid encoding at least a portion of a cellular factor(X) may be spliced to a nucleic acid sequence encoding a eukaryotic peptide(Y) by creating three oligonucleotide primers, one of which corresponds to a portion of the X sequence (the "X primer"), another which corresponds to a portion of the Y sequence (the "Y primer"), and a third which contains a portion of both X and Y sequences ("the XY primer"). It may further be desireable to incorporate useful restriction endonuclease cleavage sites in the primers. Table 3 infra, presents examples of primers which may be used to produce BDNF-NGF chimeras. these three oligonucleotides (represented in FIG. 1 by primers A, C, and B, respectively) may be combined in a one-step PCR, it being desireable that the X and Y primers are present in greater amounts than the XY primer, for example, at a ratio of X:XY:Y of about 100:1:100. The template utilized in the PCR may be a mixture of nucleic acids encoding the cellular factor and the protein or peptide to be spliced. The position of the splice site is determined by the bridging nucleotide (e.g. the XY primer). Amplification conditions routinely used in the art may be used, for example, 1 minute at about 94° C., 2 minutes at about 43° C. and 3 minutes at about 72° C. for 35 cycles, using standard PCR reaction solutions and methods. The resulting PCR fragment may then be gel purified using gel electrophoresis, cleaved with appropriate restriction endonuclease enzymes, and then inserted into a suitable vector for cloning.

Alternatively, as depicted in FIG. 2, chimeric neurotrophic factors may be produced by a three-step PCR, involving four oligonucleotides. Oligonucleotides which may, for example, be used to produce BDNF-NGF or NGF-BDNF chimeras are presented in Tables 4 and 10, respectively. To effect a splice between nucleotide sequences X and Y, the following primers may be constructed:(i) primer X, corresponding to X sequence (primer A in FIG. 2); primer Y, corresponding to Y sequence (primer D in FIG. 2); primer XY, corresponding to subsequences of both X and Y (primer B in FIG. 2); and primer XY', also corresponding to subsequences of both X and Y, but additionally homologous to primer XY (primer C in FIG. 2). In one PCR reaction, primers X and XY are amplified off of sequence X template, to produce nucleic acid comprising portions of X and Y sequence. In another PCR reaction, primers Y and XY' are amplified off of sequence X template, to produce nucleic acid sequence comprising portions of X and Y sequence which overlaps with the Y portion of the nucleic acid molecule produced in the other PCR reaction. When the products of the two PCR are combined and amplified by PCR, a nucleic acid molecule may be generated which comprises an insertion of Y sequence into X sequence. Modifications of this method using two different templates may also be utilized according to the invention. PCR, purification of PCR product, and restriction endonuclease enzyme cleavage may then be used as described supra in order to clone the resulting chimeric neurotrophic factor gene.

DNA reaction products may be cloned using any method known in the art. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, or Bluescript® (Stratagene) plasmid derivatives. Recombinant molecules can be introduced into host cells via transformation, transfection, infection, electroporation, etc.

5.3. EXPRESSION OF CHIMERIC NEUROTROPHIC FACTORS

The nucleotide sequence coding for a chimeric neurotrophic factor protein, or a portion thereof, can be inserted into an appropriate expression vector, i.e., a vector which contains the necessary elements for the transcription and translation of the inserted protein-coding sequence. The necessary transcriptional and translation signals can also be supplied by the native chimeric neurotrophic factor gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric neurotrophic factor gene consisting of appropriate transcriptional/translational control signals and the protein coding sequences. These methods may include in vitro recombinant DNA and synthetic techniques and in vivo recombinations (genetic recombination). Expression of nucleic acid sequence encoding chimeric neurotrophic factor protein or peptide fragment may be regulated by a second nucleic acid sequence so that chimeric neurotrophic factor protein or peptide is expressed in a host transformed with the recombinant DNA molecule. For example, expression of chimeric neurotrophic factor may be controlled by any promoter/enhancer element known in the art. Promoters which may be used to control chimeric neurotrophic factor expression include, but are not limited to, the cytomegalovirus (CMV) promoter, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionine gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 1:2871), and the promoter for the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing chimeric neurotrophic factor gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted chimeric neurotrophic factor gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the chimeric neurotrophic factor gene is inserted within the marker gene sequence of the vector, recombinants containing the chimeric neurotrophic factor insert can be identified by the absence of the marker gene function. In the third approach, recombinant expression vectors can be identified by assaying the foreign gene product expressed by the recombinant. Such assays can be based, for example, on the physical or functional properties of the chimeric neurotrophic factor gene product in bioassay systems as described infra, in Section 5.4.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered chimeric neurotrophic factor protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign proteinexpressed. For example, expression in a bacterial system can be used to produce an unglycosylated core protein product. Expression in yeast will produce a glycosylated product. Expression in mammalian cells can be used to ensure "native" glycosylation of the heterologous chimeric neurotrophic factor protein. Furthermore, different vector/host expression systems may effect processing reactions such as proteolytic cleavages to different extents.

In specific embodiments of the invention, DNA encoding chimeric neurotrophic factors may be expressed in a COS cell system according to methods set forth in sections 6 and 8, infra. Once a recombinant which expresses the chimeric neurotrophic factor gene is identified, the gene product should be analyzed. This can be achieved by assays based on the physical or functional properties of the product. See Section 5.4.

Once the chimeric neurotrophic factor protein is identified, it may be isolated and purified by standard methods including chromatography (e.g., ion exchange, affinity, and sizing column chromatography), centrifugation, differential solubility, or by any other standard technique for the purification of proteins.

Furthermore, chimeric neurotrophic factor proteins and peptides of the invention may be produced using standard peptide chemical synthetic techniques well known in the art.

5.4. NEUROTROPHIC FACTOR ASSAYS FOR CHIMERIC NEUROTROPHIC FACTORS

The chimeric neurotrophic factors of the invention exhibit neurotrophic activity. The term "neurotrophic activity," as used herein, should be construed to refer to a biological effect on nervous system cells, including, but not limited to, neurons, astrocytes, glial cells, oligodendrocytes, microglia and Schwann cells. The biological effect is an alteration in the structure and/or physiology of a nervous system cell which does not occur absent direct or indirect exposure to the chimeric neurotrophic factor. Examples of a biological effects are the prolongation of survival, neurite sprouting, the maintenance or development of differentiated functions (such as expression of an enzyme e.g. choline acetyltransferase or tyrosine hydroxylase) or, conversely, cell death or senescence, or dedifferentiation.

The presence of neurotrophic activity may be determined using any known assay for such activity as well as systems which may be developed in the future. Assay systems may include in vitro testing systems, such as tissue culture bioassay systems using tissue explants, cells prepared from tissue, or immortalized cell lines, for example, derived from the brain, spinal cord, or peripheral nervous system, as well as in vivo testing systems in which chimeric neurotrophic factor may be administered to an animal; neurotrophic effects may be detected in such an animal by performing, chemical, histologic, or behavioral tests using said animal. Additionally, a chimeric neurotrophic factor may be incorporated as a transgene in a non-human transgenic animal, and its biological effects may be measured in said animal.

For example, but not by way of limitation, neurotrophic activity may be measured using any of the following well known bioassay systems:

(i) dorsal root ganglia assay system, as described in Barde et al., 1980, Proc. Natl. Acad. Sci. USA. 77:1199–1203, which is incorporated by reference in its entirety herein;

(ii) nodose ganglia assay system as described by Lindsay et al., 1985, Dev. Biol. 112:319–328, which is incorporated by reference in its entirety herein;

(iii) sympathetic ganglia assay as described in Barde et al., 1982, EMBO J. 1:549–553, which is incorporated by reference in its entirety herein;

(iv) ciliary ganglia assay as described in Adler et al., 1979, Science 204:1434–1436, which is incorporated by reference in its entirety, (v) spinal cord neurons. Briefly, spinal cords may be removed aseptically from a test animal, severed caudal to the bulb, and freed of sensory ganglia and meninges. The cord may then be subdivided into ventral and mediodorsal segments for separate cultures, and the tissues minced into small pieces and dissociated by trituration through a Pasteur pipet in 50 percent DMEM (Gibco) and 50 percent Ham's nutrient mixture F12 (Gibco) supplemented with 33 mM glucose, 2mM glutamine, 15 mM NaHCO$_3$, 10 mM HEPES, 25 µg/ml insulin, 100 µg/ml transferrin, 60 µm putrescine, 20 nM progesterone, 30 nM Na selenite, 0.5 µg/ml penicillin G, 0.5 µg/nl streptomycin, and 2.5 µg/ml bovine serum albumin. Trituration may then be repeated twice and supernatants may be pooled and filtered through a 40 µm Tetko filter. Dissociated ventral cells may then be plated in on poly-D-lysine coated (10 µg/ml) culture dish at a density of 0.5 million cells per 35 mm dish. Dissociated mediodorsal cells may be plated at a density of 1.5 million cells per 35 mm dish coated with poly-D-lysine (10 µg/ml), poly-L-ornithine (10 µg/ml) or poly-L-ornithine plus laminin (5 µg/ml).

(vi) basal forebrain cholinergic neurons (refer to U.S. patent application Ser. No. 07/400,591);

(vii) ventral mesencephalic dopaminergic neurons (refer to U.S. patent application Ser. No. 07/400,591); and (viii) PC12 cells.

5.5. ANTIBODIES DIRECTED TOWARD CHIMERIC NEUROTROPHIC FACTORS

According to the invention, chimeric neurotrophic factor protein, or fragments or derivatives thereof, may be used as immunogen to generate anti-chimeric neurotrophic factor antibodies. To improve the likelihood of producing an anti-chimeric neurotrophic factor immune response, the amino acid sequence of chimeric neurotrophic factor may be analyzed in order to identify portions of the molecule which may be associated with increased immunogenicity. For example, the amino acid sequence may be subjected to computer analysis to identify surface epitopes, according to the method of Hopp and Woods (1981, Proc. Natl. Acad. Sci. U.S.A. 78:3824–3828) which has been successfully used to identify antigenic peptides of Hepatitis B surface antigen. Alternatively, the deduced amino acid sequences of chimeric neurotrophic factor from different species could be compared, and relatively non-homologous regions identified; these non-homologous regions would be more likely to be immunogenic across various species.

For preparation of monoclonal antibodies directed toward chimeric neurotrophic factor, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 1:72), and the EBV-hybridoma technique to produce human monoclonal antibodies (Cole et al , 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of chimeric neurotrophic factor. For the production of antibody, various host animals can be immunized by injection with chimeric neurotrophic factor protein, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and, *Corynebacterium parvum*.

A molecular clone of an antibody to a chimeric neurotrophic factor epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to the $F(ab')_2$ fragment which can be produced by pepsin digestion of the antibody molecule; the Fab' fragments which can be generated by reducing the disulfide bridges of the $F(ab')_2$ fragment, and the 2 Fab or Fab fragments which can be generated by treating the antibody molecule with papain and a reducing agent.

5.6. UTILITY OF THE INVENTION

The present invention provides for chimeric neurotrophic factor genes and proteins which may be utilized in various diagnostic and therapeutic applications. Chimeric neurotrophic factors of the invention include molecules which (i) combine the activity of two neurotrophic factors in a single molecule; (ii) exhibit unique spectra of activity relative to naturally occurring factors; (iii) function as superagonists of a naturally occurring factor; or (iv) function as antagonists or inhibitors of a naturally occurring factor.

Chimeric neurotrophic factors of the invention may be utilized in diagnostic applications. For example, the chimeric neurotrophic factors of the invention may comprise an antigenic peptide tag, such as a myc tag (see Section 7, infra) which may bind to labelled antibody. Such a chimeric neurotrophic factor may be bound to cells responsive to neurotrophic factor, and, by indirectly binding label, may serve as an indicator of neurotrophic factor responsive cells, a technique which may be useful in the diagnosis or study of nervous system disorders. It may be desireable to design a chimeric neurotrophic factor for diagnostic purposes which has minimal neurotrophic activity.

The present invention also provides for the use of chimeric neurotrophic factors in various therapeutic applications. Chimeric neurotrophic factors offer the advantages of, in particular instances, providing activities typically associated with several neurotrophic factors in a single molecule and/or extending the range of activity beyond that of the chimeric's parent molecule. For example, chimera NM1 comprising NGF linked to a myc antigenic peptide, exhibited activity in bioassays utilizing dorsal root ganglia, nodose ganglia, and sympathetic ganglia; in contrast, native NGF has little or no activity in nodose ganglia assays. Therefore NM1 exhibits an extended range of activity, as it exerts its effects on cell types not generally responsive to its parent molecule, NGF. This may prove to be particularly important in situations where it would be desireable to induce a response in sympathetic, parasympathetic, and sensory neurons, for example, in amyloid polyneuropathy, diabetic neuropathy, and dysautonomic polyneuropathy. Although dorsal root ganglia, sympathetic ganglia, and nodose ganglia may also respond to a combination of neurotrophins, for example BDNF and NGF, or to factor NT-3 alone, a chimeric molecule affecting all three cell types may be relatively free of side effects which may be caused by administration of BDNF plus NGF or NT-3 alone. Furthermore, chimeric neurotrophic factors may exhibit more potent activity than their naturally occurring counterparts; for example, as shown in FIG. 6, BM1, comprising portions of BDNF and a myc peptide, was found to exhibit a higher survival promoting activity than BDNF in dorsal root ganglia and sympathetic ganglia assays. NGF and BDNF have been observed to have additive neurotrophic activity; according to the invention, a single chimeric neurotrophic factor may be utilized to provide the activity of multiple parental factors in a single molecule.

In additional embodiments, chimeric neurotrophic factors may comprise a toxic component and may be used for the elimination of diseased cells responsive to the chimeric neurotrophic factor, for example, virus infected cells or tumors of nervous system origin.

In various embodiments of the invention, chimeric neurotrophic factor protein, peptide fragments or derivatives can be administered to patients in whom the nervous system has been damaged by trauma, surgery, ischemia, infection (e.g. polio or A.I.D.S.), metabolic disease, nutritional deficiency, malignancy, or toxic agents. In further embodiments of the invention, chimeric neurotrophic factor protein or peptide fragments or derivatives derived therefrom, can be used to treat congenital conditions or neurodegenerative disorders, including, but not limited to, Alzheimer's disease, ageing, peripheral neuropathies, Parkinson's disease, Huntington's chorea and diseases and disorders of motorneurons.

In a specific embodiment of the invention, administration of chimeric neurotrophic factor protein, or peptide fragments or derivatives derived therefrom, can be used in conjunction with surgical implantation of tissue or other sustained release compositions in the treatment of Alzheimer's disease, amyotrophic lateral sclerois and other motor-neuron diseases (including, for example, Werdnig-Hoffman disease), and Parkinson's disease. Alzheimer's disease has been shown to involve selective loss of cholinergic neurons in the basal forebrain, and it has been shown that approximately 35 per cent of patients with Parkinson's disease suffer from Alzheimer-type dementia; chimeric neurotrophic factor produced according to the invention may prove to be useful single agent therapy for this disease complex. Similarly, chimeric neurotrophic factor produced according to the invention may be used therapeutically to treat Alzheimer's disease in conjunction with Down's Syndrome. Chimeric neurotrophic factor produced according to the invention can be used in the treatment of a variety of dementias as well as congenital learning disorders.

In further embodiments of the invention, chimeric neurotrophic factor protein, fragments or derivatives can be used in conjunction with other cytokines to achieve a desired neurotrophic effect. The active compositions of the invention, which may comprise chimeric neurotrophic factor, including protein, peptide fragments or derivatives produced therefrom, or antibodies (or antibody fragments) directed toward chimeric neurotrophic factor protein, peptide fragments, or derivatives, or a combination of chimeric neurotrophic factor and a second agent, such as NGF may be administered in any sterile biocompatible pharmaceutical carrier, including, but not limited to, saline, buffered saline, dextrose, and water.

The amount of chimeric neurotrophic factor protein, peptide fragment, derivative, or antibody which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, e.g. in the chimeric neurotrophic factor bioassay systems described supra, and then in useful animal model systems prior to testing in humans.

Methods of introduction include but are not limited to intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Methods of introduction may also be provided by rechargable or biodegradable devices.

Further, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, nonporous, or gelatinous material, including membranes, such as sialastic membranes, or fibers.

The invention also provides for pharmaceutical compositions comprising chimeric neurotrophic factor proteins, peptide fragments, or derivatives administered via liposomes, microparticles, or microcapsules. In various embodiments of the invention, it may be useful to use such compositions to achieve sustained release of chimeric neurotrophic factor and chimeric-neurotrophic factor related products.

6. EXAMPLE:CONSTRUCTION AND EXPRESSION OF BDNF/NGF AND MYC-TAGGED CHIMERIC NEUROTROPHIC FACTORS

A number of genetically modified molecules of NGF and BDNF were constructed in order to examine whether such modifications would alter the specificity of action of NGF or BDNF. The constructs were made using polymerase chain reaction to accomplish gene splicing by overlap extension (Horton et al., 1989, Gene 77:61–68).

6.1 MATERIALS AND METHODS

6.1.1. CONSTRUCTION OF CHIMERIC MOLECULES

Protocols were designed in which chimeric molecules were produced by a one-step polymerase chain reaction utilizing three oligonucleotide primers or, alternatively, by a three-step polymerase chain reaction utilizing four oligonucleotide primers. These methods were used to produce nine chimeras, designated R2-R10, which comprise portions of BDNF and NGF encoding sequences, and two chimeras, NM1 and BM1, comprising nucleic acid encoding a portion of the myc protein "tagged" onto NGF and BDNF, respectively; the tag sequence being glu-lys-leu-ile-ser-glu-glu-asp-leu.

For chimera R1, hNGF was amplified with a 5'-oligo containing a Cla1 restriction site and a 3'-oligo containing a Not1 site. The PCR fragment was then subcloned into nar1/Not1 sites of pC8hB(P1).

The oligonucleotides used to produce chimera R1 were as follows:

5'- Oligo

5'- GCTTACCTGATCGATCATCATCCCATC-CCATCTTC

3'- Oligo

5'- GCTATGCGCCGCGGATCCTTATCATCT-CACAGCC

6.1.1.1. CONSTRUCTION OF CHIMERIC MOLECULES USING A ONE-STEP POLYMERASE CHAIN REACTION

FIG. 1 is a schematic diagram of the use of three oligonucleotides (designated A, B, and C) in a one-step polymerase chain reaction (PCR; Saiki et al, 1985, Science 230:1350–1354) to effect gene splicing by overlap extension using a modification of the method set forth in Horton et al. (1989, Gene 77:61–68). The three oligos "A", "B", and "C" were used in a 100:1:100 ratio in a one-step PCR reaction using the two templates hBDNF (expression plasmid for human BDNF in pCDMε, designated pCε-hB(P1)) and hNGF (human synthetic NGF gene purchased from British Biotechnology Ltd.). During the first few cycles, asymmetric amplification resulted in a predominantly single stranded product A-B. This subsequently was amplified with oligo C to form the fusion product A-C. Using this method, replacements of large portions of the BDNF molecule were made by fusing part of the mature BDNF molecule with part of the NGF molecule. The position of the fusion is defined by the middle oligo ("B") which was composed of NGF sequence at the 5' end and BDNF sequence at the 3' end. The amplification condition routinely used was 1 minute at 94° C., 2 minutes at 43° C. and 3 minutes at 72° C. for 35 cycles. The PCR fragment was gel purified, digested with Nar1 /Not1, and subcloned into the corresponding sites of pC8hB(P1). This method was used to construct chimeras R2-5 (designated pC8hB/hN-R1 to pC8hB/hN-R5). Table 3 presents the three oligonucleotides used to produce chimeras R2, R3, R4, and R5, including the 5' oligonucleotide (corresponding to primer A in FIG. 1), the middle oligonucleotide (corresponding to primer B in FIG. 1), and the 3' oligonucleotide (corresponding to primer C in FIG. 1).

TABLE 3

Oligonucleotide Primers Used In Construction Of R2, R3, R4 And R5 Chimeras

CHIMERA R2

5' - Oligo
5' - GATGCTGCAAACATGTCCATG
Middle Oligo
5' - CTTATCCCCAACCCACACGCTAATACTGTCACACACGC
3' - Oligo
5' - GCTATGCGGCCGCGGATCCTTATCATCTCACAGCC
The same 5' - oligo and 3' - oligo were used for Chimera R3 to R5

CHIMERA R3

Middle oligo
5' - GACGGGATTTGGGTCCCGGCACTTGGTCTCGTAGAAG

CHIMERA R4

Middle Oligo
5' - GAGTTCCAGTGCTTTGAGTCTATGCCCCTGCAGCC

CHIMERA R5

Middle oligo
5' - GACAAAGGTGTGAGTCGTTCGGCACTGGGAGTTCCAATG

6.1.1.2. CONSTRUCTION OF CHIMERIC MOLECULES USING A THREE-STEP POLYMERASE CHAIN REACTION

FIG. 2 is a schematic diagram of the use of four oligonucleotides (designated A, B, C, and D) in a three-step PCR reaction to effect gene splicing by overlap extension. Because primers B and C comprised a portion of NGF sequence, the final reaction products were chimeric molecules in which a relatively small subsequence of BDNF was substituted by NGF sequence.

As shown in FIG. 2, hBDNF in a BLUESCRIPT vector (Stratagene) was amplified with the 5' oligo (A) and middle oligo (B), while hBDNF in pCDM8 was amplified with the middle oligo (C) and 3'-oligo (D). These two PCR fragments were gel purified, and aliquots were combined in a subsequent reaction. Since the two middle oligonucleotides contained overlapping NGF sequences at their 5' end, the two PCR fragments A-B and C-D were able to hybridize to each other in the overlapping region and could therefore be amplified with the 5' and 3' oligonucleotide to result in a PCR fragment that contained a small substitution by NGF. This fragment was digested with Nar1 /Not1 and was cloned into the corresponding sites in pC8-hB(P1). Using two BDNF templates cloned in different vectors as starting material, each with a unique end-oligo (primer A and D, respectively), circumvented the likelihood of obtaining false negatives. This method was used to construct chimeras R6–10 (designated pC8hB/hN-R6, pC8hB/mN-R7 to pC8hB/mN-R10). For chimera R6, pBS-hB was used as the template for primers A and B whereas synthetic hNGF was used as the template for primers C and D.

Table 4 presents the oligonucleotide primers used in the construction of chimeras R6, R7, R8, R9 and R10.

TABLE 4

Oligonucleotides Used In Construction of R6, R7, R8, R9 and R10 NM1 and BM1 Chimeras

CHIMERA R6

5' - Oligo (A)
5' - GATGCTGCAAACATGTCCATG
Middle Oligo (B)
5' - GCCTTTCTAGAGAGCACACATACACAAGAAGTGTC
Middle Oligo (C)
5' - GTGCTCTCTAGAAAGGC
3' - Oligo (D)
5' - GCTATGCGGCCGCGGATCTTATCATCTCACAGCC-3'

CHIMERA R7

5' - Oligo (A)
5' - GTAAAACGACGGCCAGT-3'
Middle Oligo (B)
5' - CAGCACTGTCACCTCCTTGCCCGACATGTCCACTGC
Middle Oligo (C)
5' - AAGGAGGTGACAGTGCTGGCCGAGGTCCCTGTATCAAAAGGC-3'
3' - Oligo (D)
5' - CAAAGATCCTCTAGAGTCGC-3'
The same 51 and 31 oligo were used for Chimera R8-R10

CHIMERA R8

Middle Oligo (B)
5' - TCTGAATACACTGTTGTTAATAGGGACCTTTTCAAGGAC-3'
Midle Oligo (C)
5' - ATTAACAACAGTGTATTCAGACAATACTTCTACGAGACC-3'

TABLE 4-continued Oligonucleotides Used In Construction of R6, R7, R8, R9 and R10 NM1 and BM1 Chimeras

CHIMERA R9

Middle Oligo (B)
5' - AACAGGATTGGAGGCTCGGCACTTGGTCTCGTAGAA
Midle Oligo (C)
5' - CGAGCCTCCAATCCTGTTGAGAGTGGCTGCAGGGGGCATAG
CHIMERA R10

Middle Oligo (B)
5' - GTATGAGTTCCAGTGTTTGGAGTCTATGCCCCTGCAGCC
Middle Oligo (C)
5' -TCCAAACACTGGAACTCATACTGCCGAACTACCCAGTCG
NM 1

5' -Oligo
5' -CGGTACCCTCGAGCCACCATGCTGTGCCTCAAG-3'
Middle Oligo
5' - CAGATCCTCCTCAGAAATCAGCTTTTGCTCACCTCCTCTTGTAGCCTTCCTG
3' - Oligo
5' - GCTATGCGGCCGCTACAGATCCTCCTCAGAAATC-3'
BM1

5' - Oligo
5' - CGGTACCCTCGAGCCACCATGACCATCCTTTTCCTT
Middle Oligo
5' - GCTATGCGGCCGCTACAGATCCTCCTCAGAAATCAGCTTTTGCTCACCTCCTTT
AATGGTAATGTAC-3
3' - Oligo
5' - GCTATGCGGCCGCTACAGAATCCTCCTCAGAAATC-3'

6.1.1.3. CONSTRUCTION OF CHIMERIC MOLECULES COMPRISING A MYC "TAG"

The one-step PCR reaction utilizing three oligonucleotide primers, described supra, was used to construct expression plasmids encoding NGF or BDNF tagged with a 10 amino acid antigenic peptide fragment of human myc protein (U.S. patent application Ser. No. 07/532,285, filed Jun. 1, 1990, which is incorporated by reference herein. The single step PCR technique was used to generate a PCR product containing the mouse NGF gene (from a plasmid encoding the long NGF precursor, pB15-NGF), linked, through a bridge encoding two glycines, to a sequence encoding the 10 amino acid myc epitope; the PCR primers were designed to result in a PCR product in which the last two codons of the native NGF genes were deleted, because of the possibility that the amino acids encoded by these codons would represent a proteolytic cleavage site that would result in loss of the myc epitope. To construct mNGF tagged with myc at the 3' end (designated pC81mN/myc-NM1), mouse NGF with long prepro (20 ng) was amplified with the 5' oligonucleotide, middle oligonucleotide, and 3' oligonucleotide at a concentration of 100, 1 and 100 ng respectively (FIG. 3A). The amplification conditions used were: 1 minute at 94° C., 2 minutes at 43° C. and 3 minutes at 72° C. for 35 cycles. The resulting PCR product was then digested with Xho1/Not1, and cloned into Xho1/Not1 digested CDM8 vector. BDNF tagged with myc epitope at the 3' end (designated pC8hB/myc-BM1) was constructed using a similar strategy (FIG. 3B).

A similar technique was used to generate PCR product containing human BDNF gene linked, through a bridge encoding two glycines, to a sequence encoding the 10 amino acid myc epitope; as with the NGF/myc chimera, the PCR primers were designed to result in a PCR product in which the last three codons of the native BDNF gene were deleted, because of the possibility that the amino acids encoded by these codons would represent a proteolytic cleavage site that would result in loss of the myc epitope. The PCR product was then digested with Nar1 /Not1 and subcloned into the parental human BDNF expression plasmid, pC8hB(P1), to generate the expression plasmid pC8hB/myc(BM1).

6.1.2. TRANSFECTION OF CHIMERIC NEUROTROPHIC FACTOR EXPRESSION CONSTRUCTS AND EXPRESSION IN COS CELLS

Plasmid DNA for each of the mammalian expression constructs described supra was prepared by double banding over a cesium chloride gradient. Purified plasmid DNA was then transfected by the calcium phosphate coprecipitation method (Chen and Okayama, Mol. Cell. Biol. 7:2745 (1987)) into COS-M5 cells. COS-M5 cells were seeded into 60 mm plates 24 hours prior to transfection at a density of $5 \times 10^5$ cells per plate in 2.5 ml of Dulbecco's modified Eagle's medium containing glucose (4500 ug/ml) and 10% fetal bovine serum. The media from the transfected cells was harvested 48 hours after transfection for bioassay. Metabolic labelling was also performed at this time (infra).

6.1.2.1. METABOLIC LABELLING 48 hours following transfection, COS-M5 cells were placed in 3 ml of DMEM (serum-free) without methionine and cysteine and containing insulin, transferrin, and selenium. The cells were amino acid-starved for 1 hour at 37 C. in 5% $CO_2$. One milliliter of serum-free DMEM was removed and the COS-M5 cells were labeled with $^{35}$S-methionine and $^{35}$S-cysteine (100 uCi/ml each) for 4 hours. Labeled COS-M5 cell supernatant was collected and analyzed by SDS polyacrylamide gel electrophoresis. FIG. 4 demonstrates the resolution of metabolically labeled hBDNF, mNGF, hBDNF/myc (Chimera BM1), and mNGF/myc (Chimera NM1).

6.2. RESULTS AND DISCUSSION

Portions of NGF and BDNF genes were spliced together using overlap extension of primers in polymerase chain reaction. Chimeric molecules were produced in which relatively large (chimeras R1-R5) or small (R6-R10) regions were substituted by NGF sequences. The amino acid sequences of R1-R10 are presented in FIG. 5A-D. Chimeras R1 through R6 comprise portions of human BDNF and human NGF and chimeras R7 through R10 comprise portions of human BDNF and mouse NGF. Table 5 presents a summary of the approximate extent of BDNF and NGF sequences in chimeras R1 through R10.

TABLE 5

| Chimera | BDNF Sequence | NGF Sequence |
|---|---|---|
| R1 | preprosequence | full mature sequence |
| R2 | preprosequence residues 1–17 | residues 18–120 |
| R3 | preprosequence residues 1–58 | residues 59–120 |
| R4 | preprosequence residues 1–72 | residues 73–120 |
| R5 | preprosequence residues 1–81 | residues 82–120 |
| R6 | preprosequence residues 1–110 | residues 111–120 |
| R7 | preprosequence residues 1–33 residues 42–118 | residues 34–41 |
| R8 | preprosequence residues 1–43 residues 51–118 | residues 44–50 |
| R9 | preprosequence residues 1–58 residues 67–118 | residues 59–66 |
| R10 | preprosequence residues 1–72 residues 80–118 | residues 73–79 |

Additionally, chimeric molecules were produced which encode NGF and BDNF tagged with a 10 amino acid antigenic peptide of myc protein. The deduced amino acid sequences of NGF/myc (chimera NM1) and BDNF/myc (chimera BM1) are shown in FIG. 5A–D.

The chimeric constructs were each transfected into COS-M5 cells by calcium phosphate coprecipitation. Expression of chimeras R1-R10 is evidenced by metabolic labelling and bioactivity assays. In order to demonstrate expression of NM1 and BM1, COS cells transfected with NM1 or BM1 were metabolically labeled with [$^{35}$S]- methionine, the supernatants were subjected to polyacrylamide gel electrophoresis, and then the electrophoretically separated proteins were transferred to a nylon membrane and autoradiographed (FIG. 4). For BDNF and chimera BMI:the major labeled protein band identified was a 31 kD band corresponding to the precursor form of these proteins. By comparing the intensity of the precursor band, it is apparent that these two proteins were expressed relatively equally. This 31 kD protein band is not present in the COS-MOCK lane (lane 1). For NGF and chimera NM1, equal expression of the mature forms of these proteins (approximately 12.5 kD) was observed. As expected, myc-tagged NGF (NM1) migrated slightly slower than NGF. All of the BDNF/NGF chimeras (R1-10) expressed predominately the 31 kD precursor protein at levels similar to BDNF.

7. EXAMPLE: NEUROTROPHIC ACTIVITY OF CHIMERIC NEUROTROPHIC FACTORS R1-R10, BM1 AND NM1

7.1 MATERIALS AND METHODS

7.1.1. BIOASSAYS USING TISSUE EXPLANTS

All chimeras (R1-R10 as well as BM1 and NM1) and including native BDNF and NGF were expressed in COS-M5 cells as described above. Supernatants harvested from transfected cells were bioassayed using tissue explants and dissociated cell cultures for their ability to induce neurite outgrowth of specific ganglia.

The activity of the chimeras was assessed by measuring the survival of cultured dissociated cells from dorsal root ganglion (DRG) or sympathetic chain ganglia (SG). Briefly, the ganglia were dissected from E8-9 chick embryos, and collected in serum-containing medium (DMEM supplemented with 10% FBS, streptomycin, penicillin and glutamine). Following trypsinization with 0.5% trypsin (Worthington), cells were gently triturated and then preplated on 60 mm uncoated plastic dishes. The preplating step (2-3 h) allowed non-neuronal cells to attach. Neuronal cells not attached were then pooled together, spun, resuspended in serum-containing medium and counted by hemocytometer. Survival of neurons can be assessed by either quantitation of cell number or by means of a colorimetric assay based on the conversion of MTT (3-(4, 5-dimethylthiazol-2-yl)- 2,5-diphenyl tetrazolium bromide) to a purple product by vital cells. For cell counts method, cells were plated at a density of 24,000 cells/35 mm dish, and cultured for 48 h in the presence or absence of COS supernatant containing expressed chimera protein prior to cell count determination. For MTT method, cells were plated at a density of 1000 cells/A2 well. At 40 h after plating, MTT dye was added at a concentration of 0.5 mg/ml. Dyes taken up by vital cells were solubilized by the addition of 0.08N HCl in isopropanol 8 hours later, and absorbance (570–650 nm) was measured. Absorbance was plotted as a function of various dilutions of COS supernatant added.

7.1.2. PC12 CELL BIOASSAYS

COS-M5 cell supernatants from transfected cells were harvested 48 hours after transfection for analysis in the PC12 cell differentiation assay. PC12 cells were seeded into 24-well plates (Costar) at a density of $1 \times 10^5$ cells per well. PC12 cells were cultured in RPMI 1640 with 6% fetal calf serum and 6% horse serum. COS supernatants were added to the PC12 cell cultures (1 ml total volume) at various dilutions between 1:5 and 1:500. Neurite outgrowth was scored as either + (most of the cells express neurites), or – (very few, if any, cells expressed neurites).

7.2. RESULTS AND DISCUSSION

7.2.1. EXPLANT ASSAYS AND DISSOCIATED CELL CULTURES

In vitro assays using explants of chick peripheral ganglia have been used to distinguish between the bioactivities of NGF and BDNF. Whereas both factors act on populations of sensory neurons found in dorsal root ganglia (DRG), derived from the neural crest, only BDNF supports the sensory neurons of the neural placode-derived nodose ganglion (NG). In contrast, NGF, but not BDNF, can support the survival and growth of neurons of the paravertebral chain sympathetic ganglia (SG). We have used these in vitro ganglia assays to determine whether specific chimeric constructs express BDNF, NGF or BDNF and NGF bioactivities.

Chimeras R7, R8, R9, R10, BM1, and NM1 were tested for neurotrophic activity in dorsal root ganglion, nodose ganglion, or sympathetic ganglia explant assay.

As demonstrated previously, both NGF and BDNF promote neurite growth from E8 chick dorsal root ganglia (DRG). Only BDNF expressed neurite outgrowth activity when assayed with nodose ganglia (NG) and NGF, but not BDNF, expressed activity with sympathetic ganglia (SG; Table 6). BDNF/NGF chimera R8 promoted neurite outgrowth from both DRGs and SGs characteristic of an NGF-like bioactivity.

Of the chimeras tagged with a 10 amino acid epitope of the c-myc proto-oncogene, BM1 expresses SG activity characteristic of an NGF-like activity while NM1 expressed some activity on NG characteristic of a BDNF-like activity (Table 6).

TABLE 6

Comparison of BDNF, NGF, BDNF/NGF chimeras and myc-tagged neurotrophic factor as assayed on explanted embryonic chick dorsal root ganglia (DRG), nodose ganglia (NG) and sympathetic ganglia (SG).

| Chimeras | DRG | NG | SG |
| --- | --- | --- | --- |
| R7 (250 ul) | 3 | 1 | 0 |
| R8 (250 ul) | 3–4 | 2 | 3 |
| R9 (250 ul) | 2–3 | 2 | 0 |
| R10 (250 ul) | 3–4 | 2 | 0 |
| NGF | 5 | 1 | 5 |
| BDNF | 3 | 2 | 0.5 |
| pCDM8 control (250 ul) | 0–1 | 0.5 | 0.5 |
| BM1 (250 ul) | 2–3 | 2 | 1–2 |
| NM1 (100 ul) | 5 | 3 | 5 |

Scores reflect the degree of neurite outgrowth and arborization observed where 5 is a maximal score and 0 is no neurite outgrowth. Scores are representative of three independent experiments. Neurite outgrowth was scored between 24 and 48 hours after the addition of neurotrophic factor.

Table 8 shows in a dose response study that with regard to induction of neurite outgrowth, NM1 was found to have activity comparable to NGF in dorsal root ganglia and sympathetic ganglia assays, but was more active in nodose ganglion assays. Regarding myc-tagged NGF, Table 7 shows that NM1 rescued approximately 63 percent of dorsal root ganglia neurons at 50 µl, whereas NGF was found to rescue only approximately 47 percent, indicating that NM1 may function as an agonist of NGF regarding neuron survival.

FIG. 6 shows the result of a colorimetric assay with MTT on DRG and SG neurons exposed to BDNF, NG, or BMI. As shown in FIG. 6, the survival promoting activity of BM1 was significantly higher than that of BDNF in both DRG and SG. Similar to NGF, the activity in both DRG and SG was not titrated out even at a 1:1000 dilution of the BM1 COS supernatant. Thus, the 3' myc tagging of the BDNF molecule endows it with SG activity.

TABLE 7

Comparison of NGF and NM1 Activity As Assayed On The Survival of Dissociated DRG Neurons From E8 Chick Embroys

| | | Number of DRG Neurons |
| --- | --- | --- |
| NGF | 5 µl | 336 |

TABLE 7-continued

Comparison of NGF and NM1 Activity As Assayed On The Survival of Dissociated DRG Neurons From E8 Chick Embroys

| | | Number of DRG Neurons |
| --- | --- | --- |
| | 20 µl | 440 |
| | 50 µl | 408 |
| NM1 | 5 µl | 334 |
| | 20 µl | 446 |
| | 50 µl | 542 |

The number of DRG neurons counted represents 3.6% of total area, and is the average of results from two dishes. NGF COS sup rescues approximately 47% of DRG neurons at 50 µl; at equivalent volume, NM1 rescues approximately 63% of the neurons.

TABLE 8

Comparison of NGF and NM1 Activity As Assayed on Explants of E8 Chick DRG, NG and SCG

| | | DRG | NG | SCG |
| --- | --- | --- | --- | --- |
| NGF | 5 µl | 1 | 2 | 2 |
| | 10 µl | 4 | 0.5–1 | 2–3 |
| | 20 µl | 4–5 | 0.5–1 | 3–4 |
| | 30 µl | 5+ | 1–2 | 4–5 |
| | 40 µl | 5+ | 0 | 5+ |
| | 60 µl | $5+^2$ | 0 | $5+^2$ |
| NM1 | 5 µl | 1–2 | 1–2 | 0–0.5 |
| | 10 µl | 2 | 2–3 | 0.5–1 |
| | 20 µl | 3–4 | 3–4 | 2–3 |
| | 30 µl | 4–5 | 4–5 | 5 |
| | 40 µl | 5+ | 5+ | 5+ |
| | 60 µl | $5+^2$ | $5+^3$ | $5+^2$ |

Neurite outgrowth was scored 24 hours after the addition of neurotrophic factor.

7.2.2. PC12 BIOASSAYS

Rat PC12 cells have been shown to differentiate in response to a number of agents including nerve growth factor. The differentiative response induced by nerve growth factor is associated with a cessation of cell proliferation and the outgrowth of long neuritic extensions. Therefore, this differentiation assay has been useful for identifying molecules with a nerve growth factor-like activity. We tested all our chimeric constructs and native BDNF and NGF for their ability to induce neurite outgrowth of PC12 cells.

As indicated in Table 9, NGF had significant neurite promoting activity even at a dilution of 1:250. NM1 was also active at a 1:250 dilution. Chimera R8 (which expressed activity on sympathetic ganglion—see Table 1) was capable of inducing PC12 cell neurite outgrowth at a 1:50 dilution. Surprisingly, similar results were also obtained for BM1 indicating that BM1 exhibited a neurotrophic activity absent in the parental molecule, BDNF. BDNF only expressed weak neurite outgrowth activity on PC12 cells at dilutions of 1:5. COS-MOCK was not active. Chimeras R1–5 and R7, R9, and R10 were not active.

Thus, in assays on both tissue explants and PC12 cells, the addition of unrelated sequences onto the C terminus of the BDNF and NGF molecule confer novel biologicl activity not present in the parental molecules.

TABLE 9

PC12 Cell Bioassay with Chimeras

| Chimeras | 1:5 | 1:25 | 1:50 | 1:100 | 1:250 | 1:500 |
|---|---|---|---|---|---|---|
| COS-MOCK | − | − | − | − | − | − |
| BDNF | +/− | − | − | − | − | − |
| NGF | + | + | + | + | + | + |
| NM1 | + | + | + | + | + | + |
| BM1 | + | + | + | − | − | − |
| R8 | + | + | + | − | − | − |

PC12 cells were scored for neurite outgrowth between 24 and 48 hours after the addition of neurotrophic factor.

8. EXAMPLE:CONSTRUCTION AND EXPRESSION OF NGF/BDNF CHIMERIC NEUROTROPHIC FACTORS

Chimeric neurotrophic factors were constructed in which regions of NGF were substituted with the corresponding region of BDNF.

8.1. MATERIALS AND METHODS

8.1.1. CONSTRUCTION OF CHIMERIC MOLECULES

NGF/BDNF chimeras were constructed by a three-step PCR reaction involving four oligonucleotides, as described in Section 6.1.1.2, supra. In each case, the outermost primers (corresponding to A and D in FIG. 2 and FIG. 7) were oligonucleotides T7 and T3 (Stratagene). FIG. 7 is a schematic diagram of the strategy used in constructing the chimeras, and Table 10 presents the sequences of the oligonucleotide primers corresponding to primers B and C in FIG. 7. The sequence of the T3 primer is 5'-ATTAACCCTCA CTAAAG-3' and of the T7 primer is 5'-AATACGAC TCAC-TATAG-3'. Briefly, the cDNA encoding mouse beta NGF was cut at its original SmaI and PstI sites (Scott et al., 1983, Nature 302:538) and subcloned into the SmaI/PstI restriction sites of pKS (Stratagene). The resulting plasmid KS-NGF served as template for all the following PCR amplifications.

Chimeric molecules were constructed by amplifying a 5' fragment using the T7 primer together with an oligonucleotide primer spanning the desired parts of NGF and BDNF. A 3' fragment was then amplified using the T3 primer and a second designed NGF/BDNF primer. The two resulting fragments were isolated and gel purified. In a second PCR-amplification step, 100–300 ng of each fragment were pooled, fused and amplified using T7 and T3 primers. All PCR reactions were carried out under the following conditions.

Denaturation was carried out for 3 minutes at 94° C. followed by 25 cycles of denaturation/renaturation consisting of 1 minute at 94° C., 2 minutes at 50° C., and 3 minutes at 72° C. Extension was then allowed to proceed for 10 minutes at 72° C. A PCR Gene-Amp Kit (Cetus) was used according to the manufacturer.

The amplified fragments were then cut with Eco RI and Sac II and subcloned into the corresponding restriction sites of a modified pBJ-5 expression vector comprising the SR alpha promoter (FIG. 8A; Takebe et al., 1988, Mol. Cell. Biol. 8:466). However, in Chimera I, Not 1 was used instead of Sac II for subcloning because an internal Sac II site had been created. All chimeras were sequenced over the entire amplified region using the Sequenase protocol (Stratagene).

TABLE 10

Olgonucleotide Primers Used In Construction of CH1-12 Chimeras

CHIMERA S-1

Primer 1(B) NGF(Δ3-9) —>BDNF 1–7 (33-mer)
5'-CGGGCGGGGTCCGAGTGGGATGAGCGCTTGCTC
Primer 2(C) (33-mer)
5' - CG GAC CCC GCC CGC CGC GGG GAG TTC TCA GTG T - 3'

CHIMERA S-2

Primer 3(B) NGF(Δ-22) —>BDNF 8–20 (37 mer)
5' - AAT GCT CTC GCA CAC GCT CAG CTC CCC CAT GTG GAA G - 3'
Primer 4(C) (39-mer)
5' - C GTG TGC GAC AGC ATT AGC GAG TGG GTT GGA GAT AAG AC-3'

CHIMERA S-3

Primer 5(B) NGF(Δ)23-33) -- .BDNF 21–33 (45 mer)
5' - C CAC TGC CGT CTT TTT ATC CGC CGC CGT AAC CCA CAC ACT GAC AC - 3'
Primer 6(C) (44 mer)
5' - T AAA AAG ACG GCA GTG GAC ATG TCG GGT AAG GAG GTG ACA GTG C - 3'

CHIMERA S-4

Primer 7(B) NGF (Δ34-42) --.BDNF (34-42) (38 mer)
5' - T TTC GAG GAC CGT GAC CGT GCC GCC CTT GAT GTC TGT G-3'
Primer 8(C) (41 mer)
5' - GTC ACG GTC CTC GAA AAA GTC AAC ATT AAC AAC AGT GTA TT - 3'

CHIMERA S-5

Primer 9(B) NGF (Δ43–50) --.BDNF (43–50) (30 mer)
5' - GCC TTT CGA GAC GGG CAC CTC GGC CAG CAC - 3'
Primer 10(C) (42 mer)

TABLE 10-continued

Olgonucleotide Primers Used In Construction of CH1-12 Chimeras

5' - CCC GTC TCG AAA GGC CAA CTG AAG CAG TAC TTT TTT
GAG ACC - 3'
CHIMERA S-6 (21-mers)

Primer B NGFTYR-54A: 5'-CAG TAC TTT TAT GAG ACC AAG - 3'
Primer C NGFTYR-54B: 5'-CTT GGT CTC ATA AAA GTA CTG - 3'
CHIMERA S-7

Primer 11(B) (38-mer)
5' - TT TGT GTA CCC CAT AGG ATT GCA CTT GGT CTC AAA
AAA-3'
Primer 12(C) (35-mer)
5' - CCT ATG GGG TAC ACA AAG GAG GGG TGC CGG GGC AT-3'
CHIMERA S-8

Primer 13(B) (32-mer)
5' - GGA GTT CCA GTG CCT CTT GTC GAT GCC CCC GC-3'
Primer 14(C) (35-mer)
5' - AGG CAC TGG AAC TCC CAG TGC ACC ACT ACT CAC A-3'
CHIMERA S-9

Primer 15(B) (37-mer)
5' - AC ATA CGA CTG GGT AGT TCG GCA GTA TGA GTT CCA
GT-3'
Primer 16(C) (37-mer)
5' - ACT ACC CAG TCG TAT GTG CGG GCG TTG ACA ACA
GAT G-3'
CHIMERA S-10

Primer 17(B) (36-mer)
5' - AT TCG TTT TTT GCT ATC CAT TGT CAA CGC CTT
GAC G-3'
Primer 18(C) (38-mer)
5' - TG GAT AGC AAA AAA CGA ATT GGC TGG AGG TTC
CGG-3'
CHIMERA S-11 (21-mers)

(B) NGFSER-108A: 5' - G ATA GAC ACT TCC TGT GTG TG-3'
(C) NGFSER-108B: 5' - CA CAC ACA GGA AGT GTC TAT C-3'
Primer 19(B) (37-mer)
5' - TCC CCT CTT AAT GGT CAA AGT ACA CAC ACA GGC
TGT G-3'
Primer 20(C) (36-mer)
5' - TG ACC ATT AAA AGG GGA AGA TGA CTT GCC TGC
AGG A-3'****

8.1.2. EXPRESSION OF CHIMERIC NEUROTROPHIC FACTORS IN COS CELLS

COS-7 cells were transfected with chimeric constructs using a DEAE-Dextran-Chloroquine method. Briefly, cell cultures were split one day before transfection so that there were about 750,000 cells per 60 mm culture dish. A transfection mix was prepared that contained 5 ul of DNA (about 5 ug), 1 ml DMEM (no serum), and 25 ul of 20 mg/ml DEAE-Dextran. Cultured COS-7 cells were then washed three times with 5 ml serum-free DMEMo The transfection mix (supra) was added, and incubated for 30 minutes at 37'C. 2 ml of serum-free DMEM were then combined with 20 ul 8 mM chloroquine, and added directly to the COS-7 cell/DNA/DEAE-Dextran mixture, which was subsequently incubated for 2 hours 30 minutes at 37'C. The supernatant was then aspirated from the cells and replaced with 2 ml serum-free DMEM containing 10% dimethylsulfoxide (DMSO). The cells were then incubated at room temperature for 2 minutes 30 seconds, after which they were washed with 5 ml DME, which was aspirated off, and replaced by about 2.5 ml of fresh DMEM plus 6% horse serum and 6% iron supplemented calf serum. Cells were then assayed for expression of chimeric neurotrophic factors after 48 to 72 hours, as set forth below.

8.2. RESULTS AND DISCUSSION

Chimeric nucleic acid molecules were produced in which portions of DNA encoding NGF were replaced by corresponding regions of BDNF at regular intervals. Table 11 presents the NGF region deletion together with the corresponding BDNF region insertion for each chimera. Note that S-6 and S-11 carry only point mutations which were also generated by three-step PCR.

TABLE 11

| CHIMERA | NGF REGION DELETION | | BDNF REGION INSERTION |
|---|---|---|---|
| | Thr Met | | His Arg |
| S-1 | NGF (Δ 3-9 | / | BDNF 1-7) |
| | Gly Val | | Gly Val |
| S-2 | NGF (Δ 10-22 | / | BDNF 8-20) |
| | Gly Gly | | Thr Gly |
| S-3 | NGF (Δ 23-33 | / | BDNF 21-33) |
| | Lys Val | | Gly Val |
| S-4 | NGF (Δ 34-42 | / | BDNF 34-42) |
| | Asn Arg | | Pro Lys |
| S-5 | NGF (Δ 43-50 | / | BDNF 43-50) |
| | Glu Cys | | Glu Cys |
| S-6 | NGF (Δ 51-58 | / | BDNF 51-58) |

TABLE 11-continued

| CHIMERA | NGF REGION DELETION | BDNF REGION INSERTION |
|---|---|---|
| S-7 | Arg Cys<br>NGF (Δ 59-68 / | Asn Cys<br>BDNF 59-68) |
| S-8 | Arg Cys<br>NGF (Δ 69-80 / | Arg Cys<br>BDNF 69-80) |
| S-9 | Thr Thr<br>NGF (Δ 81-91 / | Arg Thr<br>BDNF 81-91) |
| S-10 | Thr Phe<br>NGF (Δ 92-101 / | Met Phe<br>BDNF 92-102) |
| S-11 | Ile Cys<br>NGF (Δ 102-110 / | Ile Cys<br>BDNF 103-111) |
| S-12 | Val Gly<br>NGF (Δ 111-120 / | Thr Arg<br>BDNF 112-119) |

The regions of substitution of BDNF sequence are presented graphically in FIG. 9, and the amino acid sequences of S1-12 are presented in FIG. 10. Note that S1-12 each comprise portions of mouse NGF coding sequence and human BDNF coding sequence.

The chimeric neurotrophic factors S1–12 were each transfected into COS-7 cells using a DEAE-Dextran-Chloroquine method. Expression of chimeric neurotrophic factors was measured by metabolic labeling with [$^{35}$S]-methionine followed by polyacrylamide gel electrophoresis of labeled cell supernatant and autoradiography. Data is given in Table 12 as percent relative to wild-type NGF. The data is generated by comparing labelling intensities of autorads specifically focusing on the mature NGF band at approximately 13 kd (FIG. 8B and C) and after immunoprecipitation of wild type NGF and NGF/BDNF chimeras using anti-NGF antibodies (FIG. 8D and E).

9. EXAMPLE:NEUROTROPHIC ACTIVITY OF CHIMERIC NEUROTROPHIC FACTORS S 1-12

9.1. MATERIALS AND METHODS

Bioassays utilizing dorsal root ganglia (DRG), sympathetic ganglia (SG), nodose ganglia (NG), and the PC12 pheochromacytoma cell line were performed essentially as described in section 7, supra.

9.2. RESULTS

The NGF activity of chimeras S1-12 was first assessed using PC12 cells. PC12 neurite outgrowth was used as a measure of NGF activity. The activity of each chimera was determined relative to the activity of recombinant wild type NGF (NGF-wt), expressed by transfected COS-7 cells which was arbitrarily assigned an expression value of 100 percent (Table 12). The specific activity for each chimera was determined by estimating chimeric neurotrophic factor concentration using SDS-PAGE analysis of metabolically-labeled transfected COS-7 cell supernatants, again arbitrarily assigning a value of 100 percent to neurotrophic activity associated with COS-7 cells transfected with NGF-wt.

Explant cultures of dorsal root ganglia (DRG), nodose ganglia (NG), and sympathetic ganglia (SG) obtained from E8 chick embryos were then exposed to equal amounts of S1-12, NGF-wt, and vector (negative contol) transfected COS-7 cell supernatants. After 24 hours in culture fiber outgrowth in response to recombinant wild type NGF, vector negative control, or chimeras S1-12 was determined (Table 12) on an arbitrary scale of 0 to 5 by comparisons to a set of standard photographs taken from a standard dose response of E8 chick DRG to NGF in the dosage range of 0 to 20 ng/ml. A score of 0 indicates no response; a score of 1 indicates detectable activity with an outgrowth of about 10 to 50 fibres (equivalent to a typical response to 20–100 picograms/ml NGF); a score of 2 indicates moderate activity, with an outgrowth of many fibers in an obvious halo; a score of 3 indicates good activity, with an outgrowth of many long fibers; a score of 4 indicates strong activity, with an abundant outgrowth of fibers, and a score of 5 indicates massive fiber outgrowth, equivalent to a maximal response to saturating levels of NGF (about 1–10 nanograms/ml). The explant results in Table 12 represent the maximum fiber outgrowth seen at saturating levels of each supernatant determined in a dose-responsive assay. Supernatants were assayed over the range of 0.1 to 83 μl in a final volume of 2 ml. In other explant studies, higher concentrations of S4 were associated with higher outgrowth scores.

TABLE 12

List of Supernatants Included:

| Clones | Relative Expression Level | Specific Activity on PC12 Cells | Explant Data* | | |
|---|---|---|---|---|---|
| | | | DRG | NG | S.C. |
| NGF-wt | 100% | 100% | 5 | 1 | 5 |
| Vector | — | — | 0 | 0 | 0 |
| S-1 | 200% | 25% | 5 | 1 | 5 |
| S-2 | 100% | 100% | 5 | 2 | 5 |
| S-3 | 100% | 100% | 5 | 3 | 5 |
| S-4 | 20% | 100% | 1 | 1 | 1 |
| S-5 | 5% | 100% | 1 | 1 | 1 |
| S-6 | 100% | 100% | 5 | 3 | 5 |
| S-7 | 50% | 100% | 5 | 2 | 5 |
| S-8 | 100% | 100% | 5 | 2 | 5 |
| S-9 | 100% | 100% | 5 | 4 | 5 |
| S-11 | 50% | 50% | 5 | 1 | 5 |
| S-12 | 100% | 50% | 5 | 3 | 5 |

*fiber outgrowth over 24 hours

9.3. DISCUSSION

Surprisingly, the data suggest that despite the substitutions of regions of NGF with BDNF sequence, most of the NGF-BDNF chimeras retain full activity on NGF responsive cells. Equal amounts of most chimeric neurotrophic factors exhibited high levels of neurite outgrowth promoting activity on PC12 cells, which were comparable to the activity of wild type NGF. There were exceptions; S-1 appeared to be notably less active than wild-type NGF, and chimeras S-11 and S-12 were found to exhibit about 50 percent of the specific activity of NGF. However, the retention of full NGF activity in most chimeras was unexpected, as it had been predicted initially that some small minor changes in critical regions of NGF sequence might lead to a substantial loss of activity.

In addition, most chimeric neurotrophic factors discussed here were, like NGF, found to induce a maximal response on dorsal root ganglia and sympathetic ganglia explants. As shown in Table 12, virtually all chimeras tested showed maximal activity towards dorsal root ganglia and sympathetic ganglia. Chimera S-12 was found to have a specific activity 3–5 fold greater than NGF on dorsal root ganglia explants, indicating that S-12 may be a "superagonist" of NGF activity at least on some target cells. A possible explanation for the superagonist activity of S-12 may be that the substitution of BDNF sequence may have produced a conformational change in the structure of NGF which resulted in an increased affinity of S-12 for the NGF receptor or, alternatively, engendered enhanced stability of S-12 to degradative processes.

Furthermore, many of the chimeras were observed to exhibit additional activity on ganglion normally responsive to BDNF more so than NGF. NGF supports survival and neurite outgrowth from explant cultures of chick embryo dorsal root ganglion sensory neurons and chick embryo paravertebral sympathetic chain ganglia, but has no effect on explants of sensory neurons of placode-derived nodose ganglia (Lindsay et al., 1985, Dev. Biol. 112:319). Conversely, BDNF supports survival and neurite outgrowth from dorsal root ganglion explants and nodose ganglion explants but has no effect upon sympathetic ganglia. As shown in Table 12, many of the NGF-BDNF chimeric neurotrophic factors induced moderate to strong fiber outgrowth of nodose ganglia explants, indicative of BDNF-like activity. Chimeras 3, 4, 6, 9, 10, and 12 all were observed to exhibit activity on nodose ganglia which was much greater than any effect seen with NGF. It would appear, therefore, that a variety of sequence modifications, ranging from the amino terminus to the carboxy terminus of NGF, may confer BDNF-like activity or activity of other members of the neurotrophin family.

10. DEPOSIT OF MICROORGANISMS

The following cDNAs were deposited with the American Type Culture Collection in Rockville, Md.:

| Chimeric Molecule Designation | Abbreviation | Accession No. |
| --- | --- | --- |
| pBJ51mN/hB-S4 | S4 | ATCC 40859 |
| pBJ51mN/hB-S9 | S9 | ATCC 40861 |
| pBJ51mN/hB-S10 | S10 | ATCC 40858 |
| pBJ51mN/hB-S12 | S12 | ATCC 40860 |
| pC8hB/mN-R8 | R8 | ATCC 40862 |
| pC81mN/myc-NM1 | NM1 | ATCC 40864 |
| pC8hB/myc-BM1 | BM1 | ATCC 40863 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A chimeric protein which has neurotrophic activity and which consists essentially of a first neurotrophic factor, wherein about 3 to about 13 consecutive amino acids of said first neurotrophic factor are replaced by a similarly sized amino acid sequence of a second neurotrophic factor such that the resulting chimeric protein differs in sequence by at least 3 amino acids from the first neurotrophic factor.

2. A protein according to claim 1 wherein said first and second neurotrophic factors are selected from the group consisting of brain derived neurotrophic factor, ciliary neurotrophic factor, neurotrophin-3 and nerve growth factor.

3. A protein according to claim 2 wherein said first neurotrophic factor is nerve growth factor and said second neurotrophic factor is brain derived neurotrophic factor.

4. The protein of claim 3, wherein said protein is encoded by the plasmid pBJ51mN/hB-S1, or a functional equivalent thereof which encodes a chimeric protein having an amino acid sequence substantially as set forth for chimera S1 in FIG. 10.

5. The protein of claim 3 wherein said protein is encoded by the plasmid pBJ51mN/hB-S2, or a functional equivalent thereof which encodes a chimeric protein having an amino acid sequence substantially as set forth for chimera S2 in FIG. 10.

6. The protein of claim 3 wherein said protein is encoded by the plasmid pBJ51mN/hB-S3, or a functional equivalent thereof which encodes a chimeric protein having an amino acid sequence substantially as set forth for chimera S3 in FIG. 10.

7. The protein of claim 3 wherein said protein is encoded by the plasmid pBJ51mN/hB-S4, as deposited with the ATCC and assigned accession number 40859, or a functional equivalent thereof which encodes a chimeric protein having an amino acid sequence substantially as set forth for chimera S4 in FIG. 10.

8. The protein of claim 3 wherein said protein is encoded by the plasmid pBJ51mN/hB-S5, or a functional equivalent thereof which encodes a chimeric protein having an amino acid sequence substantially as set forth for chimera S5 in FIG. 10.

9. The protein of claim 3 wherein said protein is encoded by the plasmid pBJ51mN/hB-S7, or a functional equivalent thereof which encodes a chimeric protein having an amino acid sequence substantially as set forth for chimera S7 in FIG. 10.

10. The protein of claim 3 wherein said protein is encoded by the plasmid pBJ51mN/hB-S8, or a functional equivalent thereof which encodes a chimeric protein having an amino acid sequence substantially as set forth for chimera S8 in FIG. 10.

11. The protein of claim 3 wherein said protein is encoded by the plasmid pBJ51mN/hB-S9, as deposited with the ATCC and assigned accession number 40861 or a functional equivalent thereof which encodes a chimeric protein having an amino acid sequence substantially as set forth for chimera S9 in FIG. 10.

12. The protein of claim 3 wherein said protein is encoded by the plasmid pBJ51mN/hB-S10, as deposited with the ATCC and assigned accession number 40858, or a functional equivalent thereof which encodes a chimeric protein having an amino acid sequence substantially as set forth for chimera S10 in FIG. 10.

13. The protein of claim 3 wherein said protein is encoded by the plasmid pBJ51mN/hB-S12, as deposited with the ATCC and assigned accession number 40860 or a functional equivalent thereof which encodes a chimeric protein having an amino acid sequence substantially as set forth for chimera S12 in FIG. 10.

14. The protein of claim 2 wherein said first neurotrophic factor is BDNF and said second neurotrophic factor is NGF.

15. The protein of claim 14 wherein said protein is encoded by the plasmid pC8hB/hN-R7, or a functional equivalent thereof which encodes a chimeric protein having an amino acid sequence substantially as set forth for chimera R7 in FIG. 5.

16. The protein of claim 14 wherein said protein is encoded by the plasmid pC8hB/hN-R8, as deposited with the ATCC and having accession number 40862 or a functional equivalent thereof which encodes a chimeric protein having an amino acid sequence substantially as set forth for chimera R8 in FIG. 5.

17. The protein of claim 14 wherein said protein is encoded by the plasmid pC8hB/hN-R9, or a functional equivalent thereof which encodes a chimeric protein having an amino acid sequence substantially as set forth for chimera R9 in FIG. 5.

18. The protein of claim 14 wherein said protein is encoded by the plasmid pC8hB/ITN-R10, or a functional equivalent thereof which encodes a chimeric protein having an amino acid sequence substantially as set forth for chimera R10 in FIG. 5.

19. The protein of claim 1 wherein said first and second neurotrophic factors are members of the neurotrophin gene family.

20. The protein of claim 19 wherein said protein comprises four cysteine residues located at four of the following positions in the amino acid sequence of the chimeric protein:

at about amino acid 14 at about amino acid 57 at about amino acid 67 at about amino acid 79 at about amino acid 108 and at about amino acid 110, or at similar positions relative to insertions or deletions in the homologous sequence shared by members of the neurotrophin family.

21. The protein of claim 19 wherein said protein comprises five cysteine residues located at five of the following positions in the amino acid sequence of the chimeric protein:

at about amino acid 14 at about amino acid 57 at about amino acid 67 at about amino acid 79 at about amino acid 108 and at about amino acid 110, or at similar positions relative to insertions or deletions in the homologous sequence shared by members of the neurotrophin family.

22. The protein of claim 19 wherein said protein comprises six cysteine residues located at the following positions in the amino acid sequence of the chimeric protein:

at about amino acid 14 at about amino acid 57 at about amino acid 67 at about amino acid 79 at about amino acid 108 and at about amino acid 110, or at similar positions relative to insertions or deletions in the homologous sequence shared by members of the neurotrophin family.

23. The protein of claim 19 wherein said protein has a pI of between about 9 and 10.

24. The protein of claim 23 wherein said protein comprises four cysteine residues located at four of the following positions in the amino acid sequence of the chimeric protein:

at about amino acid 14 at about amino acid 57 at about amino acid 67 at about amino acid 79 at about amino acid 108 and at about amino acid 110, or at similar positions relative to insertions or deletions in the homologous sequence shared by members of the neurotrophin family.

25. The protein of claim 23 wherein said protein comprises five cysteine residues located at five of the following positions in the amino acid sequence of the chimeric protein:

at about amino acid 14 at about amino acid 57 at about amino acid 67 at about amino acid 79 at about amino acid 108 and at about amino acid 110, or at similar positions relative to insertions or deletions in the homologous sequence shared by members of the neurotrophin gene family.

26. The protein of claim 23 wherein said protein comprises six cysteine residues located at the following positions in the amino acid sequence of the chimeric protein:

at about amino acid 14 at about amino acid 57 at about amino acid 67 at about amino acid 79 at about amino acid 108 and at about amino acid 110, or at similar positions relative to insertions or deletions in the homologous sequence shared by members of the neurotrophin gene family.

27. A chimeric protein which has neurotrophic activity and which consists essentially of a portion of a member of the neurotrophin family and, the myc peptide having the sequence GLU-GLN-LYS-LEU-ILE-SER-GLU-GLU-ASP-LEU, wherein said myc peptide confers on said chimeric protein a neurotrophic activity not displayed by the neurotrophin.

28. The protein of claim 27 wherein said neurotrophic factor is BDNF.

29. The protein of claim 28 wherein said protein is encoded by the plasmid pC8hB/myc-BMI deposited with the ATCC and having accession number 40863, or a functional equivalent thereof which encodes a protein having an amino acid sequence substantially as set forth for chimera BM1 in FIG. 5.

30. The protein of claim 27 wherein said neurotrophic factor is NGF.

31. The protein of claim 30 wherein said chimeric protein is encoded by the plasmid pC81mN/myc-NMI deposited with the ATCC and having accession number 40864, or a functional equivalent thereof which encodes a protein having an amino acid sequence substantially as set forth for chimera NM1 in FIG. 5.

32. A chimeric protein having an amino acid sequence substantially as set forth for chimera S6 in FIG. 10.

\* \* \* \* \*